United States Patent [19]

Kiernan et al.

[11] Patent Number: 4,754,047
[45] Date of Patent: Jun. 28, 1988

[54] PHENYLETHANOLAMINE DERIVATIVES AND ACID ADDITION SALTS THEREOF FOR ENHANCING THE GROWTH RATE OF MEAT-PRODUCING ANIMALS AND/OR IMPROVING THE EFFICIENCY OF FEED UTILIZATION THEREBY

[75] Inventors: Jane A. Kiernan, Kendall Park; Pamela K. Baker, Hopewell, both of N.J.

[73] Assignee: American Cyanamid Company, Stamford, Conn.

[21] Appl. No.: 679,714

[22] Filed: Dec. 10, 1984

Related U.S. Application Data

[60] Division of Ser. No. 528,765, Sep. 2, 1982, Pat. No. 4,501,751, which is a division of Ser. No. 219,054, Dec. 22, 1980, Pat. No. 4,404,222, which is a continuation-in-part of Ser. No. 181,254, Aug. 25, 1980, abandoned, which is a continuation-in-part of Ser. No. 143,069, Apr. 24, 1980, abandoned, which is a continuation-in-part of Ser. No. 066,908, Aug. 16, 1979, abandoned.

[51] Int. Cl.$^4$ ............... C07C 101/00; C07C 149/40; C07C 103/28; C07C 125/06
[52] U.S. Cl. ........................... 558/422; 560/19; 560/29; 560/32; 560/33; 562/426; 562/432; 562/442; 562/451; 564/164; 564/165; 564/363; 564/340; 564/365
[58] Field of Search ............... 514/522, 523, 524, 529, 514/533, 540, 538, 562, 563, 567, 570, 571, 619, 626, 613, 653, 654; 560/19, 29, 32, 33; 562/426, 432, 442, 451; 564/164, 165, 363, 340, 365; 558/422

[56] References Cited

U.S. PATENT DOCUMENTS

| | | | |
|---|---|---|---|
| 2,754,000 | 8/1953 | Fauran et al. | 424/272 |
| 2,938,921 | 5/1960 | Mills | 564/363 |
| 3,236,892 | 2/1966 | Petracek | 564/363 |
| 3,344,188 | 9/1967 | Wollweber et al. | 564/363 |
| 3,348,999 | 10/1967 | Woroch et al. | 424/272 |
| 3,536,712 | 10/1970 | Keck et al. | 564/363 |
| 3,574,211 | 4/1971 | Keck et al. | 564/363 |
| 3,657,319 | 4/1972 | Kaiser et al. | 560/29 |
| 3,759,979 | 9/1973 | Beregi et al. | 564/164 |
| 3,869,492 | 3/1975 | Biel et al. | 560/29 |
| 3,870,715 | 3/1975 | Hansl | 562/442 |
| 3,896,141 | 7/1975 | Keck et al. | 564/363 |
| 3,954,871 | 5/1976 | Buu-Hoi et al. | 562/432 |
| 4,063,025 | 12/1977 | Murakami et al. | 560/29 |
| 4,119,710 | 10/1978 | Engelhardt et al. | 558/422 |
| 4,163,060 | 7/1979 | Hartog et al. | 564/165 |
| 4,179,442 | 12/1979 | Köllensperger et al. | 424/272 |
| 4,186,129 | 1/1980 | Huth et al. | 424/272 |
| 4,188,323 | 2/1980 | Pestellini et al. | 424/272 |
| 4,211,794 | 7/1980 | Kraska | 564/363 |
| 4,214,001 | 7/1980 | Engelhardt et al. | 560/29 |
| 4,238,506 | 12/1980 | Stach | 562/442 |
| 4,338,455 | 7/1982 | Zupan | 560/29 |
| 4,385,066 | 5/1983 | Ainsworth et al. | 562/451 |
| 4,396,627 | 8/1983 | Ainsworth et al. | 562/451 |

FOREIGN PATENT DOCUMENTS

| | | | |
|---|---|---|---|
| 2935902 | 2/1981 | Fed. Rep. of Germany | 424/272 |
| 41-6462 | 4/1966 | Japan | 564/340 |
| 7504917 | 10/1975 | Netherlands | 564/164 |

Primary Examiner—Douglas W. Robinson
Attorney, Agent, or Firm—Alice C. Brennan

[57] ABSTRACT

There is provided a method for enhancing the growth rate of meat-producing animals and/or improving the efficiency of feed utilization thereby, which involves, orally or parenterally, administering to said animals a growth-enhancing amount of a phenylethanolamine compound or the acid addition salt thereof.

10 Claims, No Drawings

PHENYLETHANOLAMINE DERIVATIVES AND ACID ADDITION SALTS THEREOF FOR ENHANCING THE GROWTH RATE OF MEAT-PRODUCING ANIMALS AND/OR IMPROVING THE EFFICIENCY OF FEED UTILIZATION THEREBY

This is a division of application Ser. No. 528,765, filed Sept. 2, 1982, which issued on Feb. 26, 1985, as U.S. Pat. No. 4,501,751, which is a division of application Ser. No. 219,054, filed Dec. 22, 1980, which issued on Sept. 13, 1983, as U.S. Pat. No. 4,404,222, which is a continuation-in-part of application Ser. No. 181,254, filed Aug. 25, 1980, now abandoned, which is a continuation-in-part of application Ser. No. 143,069, filed Apr. 24, 1980, now abandoned, which in turn is a continuation-in-part of application Ser. No. 066,908, filed Aug. 16, 1979, now abandoned.

SUMMARY OF THE INVENTION

Substitution products of 1-(amino-dihalophenyl)-2-aminoethanes, and the acid addition salts thereof, are disclosed in U.S. Pat. No. 3,536,712, issued Oct. 27, 1970. Specifically, methods for the synthesis of said compounds are disclosed as useful for enhancing the blood circulation, and as bronchodilators, analgesics, sedatives, antipyretics, antiphlogistics and antitussives in warm-blooded animals. However, only the analgesic utility is examplified. The preparation of other related 1-(amino-dihalophenyl)-2-aminoethanols and their derivatives are disclosed in Japanese Kokai No. 77 83,619 (Chemical Abstracts, 87,201061r), German Offenlegungsschrift No. 2,804,625 (1979), German Offenlegungsschrift No. 2,157,040 (1973), German Offenlegungsshrift No. 2,261,914 (1974), Europen Patent Application No. 8,715 (1980), Netherlands Patent Application No. 7,303,612 (1973). These applications disclose uses selected from analgesics, broncholytic, anti-inflammatory, uterine, spasmolytic, $\beta$-blocking activities, antispasmolytic acitvity on cross-striped muscle structure, for tocology, reducing blood pressure by peripheral vasodilation and mobilizing body fat, and for treating allergies. There is no indication or suggestion in any of these disclosures that said compounds are effective as growth-promoting agents for meat-producing animals, such as poultry, cattle, sheep or the like; nor is there any suggestion that said compounds improve the efficiency of feed utilization by said meat-producing animals.

In accordance with the process of the invention, it has been found that the growth rate of meat-producing animals such as chickens, turkeys, rabbits, sheep, goats and cattle, including calves, can be increased and/or the efficiency of feed utilization thereby measurably improved by the oral or parenteral administration to said animals of an effective amount of a compound selected from the group consisting of:

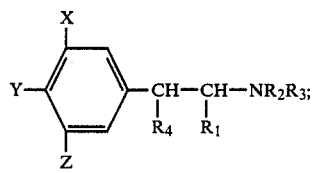
(I)

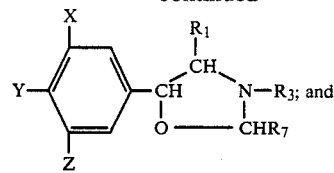
(Ia)

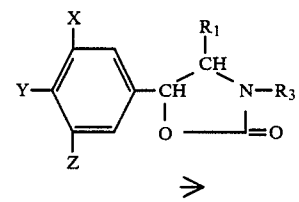
(Ib)

wherein,

X is hydrogen, halogen or —CN;

Y is hydrogen, $NR_8R_9$ or $NHCOR_5$;

Z is hydrogen, halogen, OH, CN, $CF_3$, $COOR_1$, $CONH_2$, $C_1$–$C_4$ alkyl, $C_1$–$C_4$ alkoxy, $NO_2$, $C_1$–$C_4$-dialkylaminomethyl or hydroxymethyl;

$R_1$ is hydrogen or $C_1$–$C_4$ alkyl;

$R_2$ is hydrogen, $C_1$–$C_6$ alkyl, $C_3$–$C_4$ alkenyl, $C_2$–$C_5$ alkanoyl or

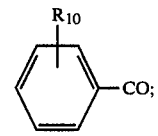

$R_3$ is hydrogen, $C_1$–$C_6$ alkyl, $C_3$–$C_6$ cycloalkyl, methoxypropyl, $C_3$–$C_4$ alkenyl, phenyl, 2-hydroxyethyl, $\alpha,\alpha$-dimethylphenethyl, benzyl, 3-phenylpropyl or 3-(4-carbomethoxyphenyl)propyl; and when $R_2$ and $R_3$ are taken together with the nitrogen to which they are attached, they represent morpholino or $N'$-$C_1$–$C_4$ alkyl-piperazino;

$R_4$ is hydrogen, OH, $OR_6$ or $SR_{11}$;

$R_5$ is hydrogen, $C_1$–$C_4$ alkyl, $C_1$–$C_4$ alkoxy,

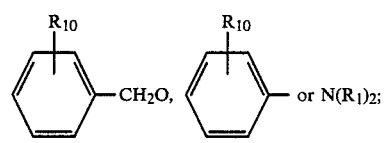

$R_6$ is $C_1$–$C_6$ alkyl, $C_2$–$C_5$ alkanoyl,

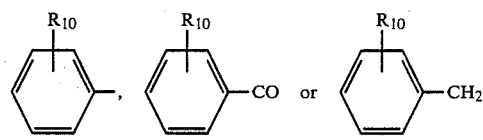

$R_7$ is hydrogen, $C_1$–$C_4$ alkyl or phenyl;

$R_8$ is hydrogen, $C_1$–$C_4$ alkyl or $C_3$–$C_4$ alkenyl;

$R_9$ is hydrogen, $C_1$–$C_6$ alkyl, $C_4$–$C_6$ cycloalkyl, $C_3$–$C_4$ alkenyl, or benzyl; and when $R_8$ and $R_9$ are taken together with the nitrogen to which they are attached, they represent pyrrolidino;

$R_{10}$ is chloro, dichloro, methyl, dimethyl, methoxy, dimethoxy or nitro;

$R_{11}$ is $C_1$–$C_6$ alkyl, phenyl or benzyl; with the provisos that when $R_3$ is phenyl, 2-hydroxyethyl, $\alpha,\alpha$-dimethylphenethyl, $C_3-C_6$ cycloalkyl, benzyl, methoxypropyl, 3-phenylpropyl, or 3-(4-carbomethoxyphenyl)propyl, $R_2$ is hydrogen; and when $R_3$ is hydroxyethyl, $R_4$ is hydroxyl and the compound is (I); and when $R_6$ is alkanoyl or

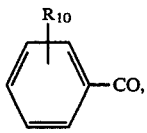

$R_2$ and $R_3$ are substituents other than hydrogen, except when $R_3$ is an alkyl or substituted alkyl group which contains a tertiary carbon attached to nitrogen; and when Y is hydrogen, X and Z are halogen, and $R_2$ is hydrogen, $C_3-C_5$ alkanoyl or

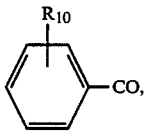

$R_3$ is isopropyl, 2-butyl, or t-butyl; and when $R_8$ is $C_1-C_4$ alkyl or $C_3-C_4$ alkenyl, $R_9$ is hydrogen, $C_1-C_4$ alkyl or $C_3-C_4$ alkenyl; and when Z is OH, X and Y are hydrogen; and that at least one of X, Y, and Z represents a substituent other than hydrogen; and when X is —CN, Z is —CN; and when Z is hydroxymethyl, $R_4$ is OH; and when Z is a group other than halogen, Y is $NR_8R_9$ or $NHCOR_5$; and when $R_5$ is $N(R_1)_2$, $R_4$ is OH; racemic mixtures of the above-identified compounds and the optically active isomers, and non-toxic, pharmacologically acceptable acid addition salts thereof.

A preferred group of compounds for use in the method of this invention have the above formula I structure wherein X is hydrogen or halogen; Y is hydrogen $NR_8R_9$ or $NHCOR_5$; Z is halogen, OH, CH, $CF_3$, $COOR_1$, $CONH_2$, methyl, methoxy, $NO_2$, $C_1-C_4$ dialkylaminomethyl, or hydroxymethyl; and the remaining groups are as hereinbefore defined; or a non-toxic, pharmacologically acceptable acid addition salt thereof.

Another preferred group of compounds for use in the method of this invention have the above formula I structure wherein X is hydrogen, chlorine, or bromine; Y is hydrogen or $NR_8R_9$; Z is chlorine, bromine, CN, $CF_3$; $R_1$ is hydrogen or methyl; $R_4$ is OH, $OR_6$, $SR_{11}$; $R_6$ is $C_1-C_6$ alkyl, benzyl, $C_2-C_5$ alkanoyl, or benzoyl; or a non-toxic, pharmacologically acceptable acid addition salt thereof.

The most preferred compounds for use in enhancing the growth rate of meat-producing animals and/or for improving the efficiency of feed utilization thereby are: 4-amino-$\alpha$-[(tert-butylamino)methyl]-3,5-dichlorobenzyl alcohol hydrochloride; 4-amino-3,5-dibromo-$\alpha$-[(diisopropylamino)methyl]-benzyl alcohol hydrochloride; 4-amino-3,5-dichloro-$\alpha$-[(diisopropylamino)methyl]benzyl alcohol hydrochloride; 4-amino-3,5-dibromo-$\alpha$-[(tert-butylamino)methyl]-benzyl alcohol hydrochloride; 4-amino-3,5-dichloro-$\alpha$-[(methylamino)methyl]benzyl alcohol hydrochloride; 4-amino-3,5-dichloro-$\alpha$-[(allylamino)methyl]benzyl alcohol; 4-amino-3-bromo-$\alpha$-[(tert-butylamino)methyl]-5-chlorobenzyl alcohol hydrochloride; $\alpha$-[4-amino-3,5-dichlorophenyl]-4-morpholineethanol hydrochloride; 4-amino-3-bromo-$\alpha$-[(tert-butylamino)methyl]-5-chlorobenzyl alcohol hydrochloride and $\alpha$-[(tert-butylamino)methyl]-3,5-dichlorobenzyl alcohol hydrochloride, 4-amino-N-tert-butyl-3,5-dichloro-$\beta$-methoxyphenethylamine hydrochloride, $\alpha$-[(tert-butylamino)methyl]-3,5-dichloro-4-methylamino-benzyl alcohol; $\alpha$-[(tert-butylamino)methyl]-3,5-dichloro-4-isopropylaminobenzyl alcohol; $\alpha$-[(tert-butylamino)methyl]-3,5-dichloro-4-ethylaminobenzyl alcohol; 5-[2-(tert-butylamino)-1-hydroxyethyl]-3-chloroanthranilonitrile; N-tert-butyl-3,5-dichloro-$\beta$-methoxy-4-methylaminophenethylamine; 3-chloro-5-[2-(tert-butylamino)-1-hydroxyethyl]anthranilonitrile;

Although it is evident from the above discussion that certain compounds represented by formula I above are described in the literature, many compounds represented by formula I are new and unobvious. The novel and unobvious compounds of the present invention are represented by the structure of formula I,

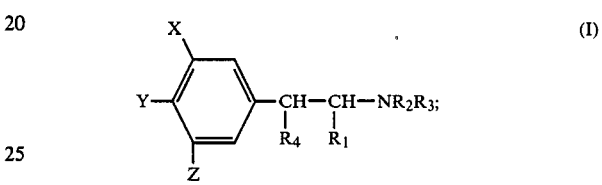

wherein
X is hydrogen, halogen or —CN;
Y is hydrogen, $NR_8R_9$ or $NHCOR_5$;
Z is halogen, —CN, $CF_3$, COOR, $CONH_2$, $C_1-C_4$ alkyl, $C_1-C_4$ alkoxy, $NO_2$ or $C_1-C_4$ dialkylaminomethyl;
$R_1$ is hydrogen or $C_1-C_4$ alkyl;
$R_2$ is hydrogen, $C_1-C_4$ alkyl, $C_3-C_6$ cycloalkyl, $C_3-C_4$ alkenyl, $C_2-C_5$ alkanoyl or

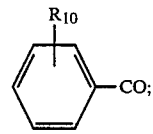

$R_3$ is hydrogen, $C_1-C_6$ alkyl, $C_3-C_6$ cycloalkyl, $C_3-C_4$ alkenyl, phenyl or benzyl;
$R_4$ is OH, $OR_6$ or $SR_{11}$;
$R_5$ is hydrogen, $C_1-C_4$ alkyl, $C_1-C_4$ alkoxy,

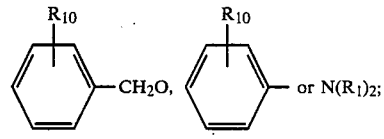

$R_6$ is $C_1-C_6$ alkyl, $C_2-C_5$ alkanoyl,

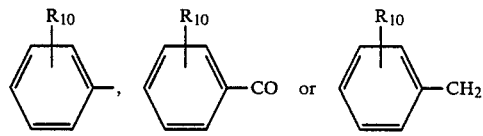

$R_8$ is hydrogen, $C_1-C_4$ alkyl or $C_3-C_4$ alkenyl;
$R_9$ is hydrogen, $C_1-C_6$ alkyl, $C_4-C_6$ cycloalkyl, $C_3-C_4$ alkenyl, or benzyl; $R_{10}$ is hydrogen, chloro, dichloro, methyl, dimethyl, methoxy, dimethoxy or nitro;

$R_{11}$ is $C_1$-$C_6$ alkyl, phenyl, benzyl; with the provisos that when Y is $NH_2$, $NHCH_3$, $NHC_2H_5$ or $NHCOR_5$, $R_4$ is $OR_6$ or $SR_{11}$; and when Y is hydrogen, X and Y are halogen, $R_2$ is hydrogen, $C_2$-$C_5$ alkanoyl or

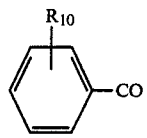

and $R_3$ is isopropyl, 2-butyl or t-butyl; and when X is —CN, Z is —CN; and when $R_6$ is alkanoyl or

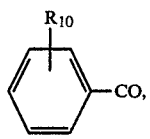

$R_2$ and $R_3$ are substituents other than hydrogen, except when $R_3$ is an alkyl or a substituted alkyl group which contains a tertiary carbon attached to nitrogen; and when $R_8$ is $C_1$-$C_4$ alkyl, or $C_3$-$C_4$ alkenyl, $R_9$ is hydrogen, $C_1$-$C_4$ alkyl or $C_3$-$C_4$ alkenyl; racemic mixtures of the above identified compounds and the optically active isomers, and non-toxic pharmacologically acceptable acid addition salts thereof.

A preferred group of the novel compounds of this invention have the above structure wherein X=hydrogen or halogen; Y is hydrogen, $NR_8R_9$, or NH—$COR_5$; Z is halogen, CN, $CF_3$, COOR, $CONH_2$, methyl, methoxy, $NO_2$, $C_1$-$C_4$ dialkylaminomethyl; $R_1$ is hydrogen, or methyl, $R_2$ is hydrogen, $C_1$-$C_4$ alkyl, $C_3$-$C_4$ alkenyl, $C_2$-$C_4$ alkanoyl or benzoyl; $R_3$ is hydrogen, $C_1$-$C_6$ alkyl, $C_3$-$C_6$ cycloalkyl, $C_1$-$C_4$ alkenyl, benzyl; with the above provisos.

A most preferred group of novel compounds of this invention have the above structure wherein X=hydrogen, chlorine, bromine; Z is chlorine, bromine, CN, $CF_3$, COOH, $COOCH_3$, $COOC_2H_5$, $CONH_2$; $R_1$ is hydrogen; $R_2$ is hydrogen, $C_1$-$C_4$ alkyl; $R_3$ is hydrogen, $C_1$-$C_4$ alkyl; with the above provisos.

It is found, that formula (I) compounds below (wherein Y is hydrogen) can be prepared by the condensation of an appropriately substituted styrene oxide with the appropriately substituted amine in the presence of an inert solvent, such as a lower alcohol at or near the boiling point of same, as shown below:

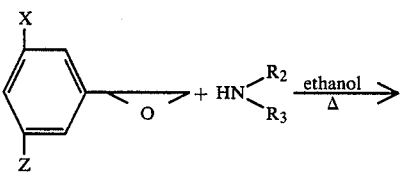

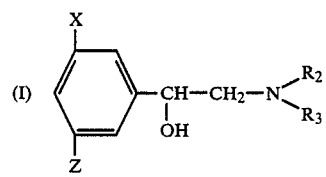

wherein X and Z are halogen, $R_2$ and $R_3$ are as hereinabove defined and Y is hydrogen. Thus, 3,5-dichlorostyrene oxide can be reacted with an equimolar or molar excess of t-butylamine in ethanol at reflux from about one to about eight hours, or until the reaction is essentially complete and the desired α-[(t-butylamino)methyl]-3,5-dichlorobenzyl alcohol is obtained as illustrated below:

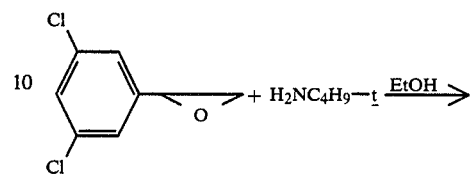

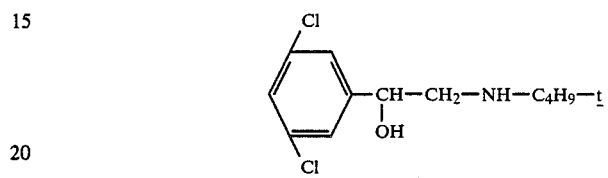

The thus obtained product can be purified by known procedures, such as chromatography or recrystallization of salts thereof.

The above styrene oxide is made by reducing the corresponding phenacyl bromide with $NaBH_4$ at or below 5° C. in the presence of an anhydrous lower alcohol, such as ethanol. The phenacyl bromide intermediate is prepared by brominating the appropriately substituted acetophenone with $CuBr_2$ in the presence of chloroform and ethyl acetate. The above sequence may be graphically illustrated as follows:

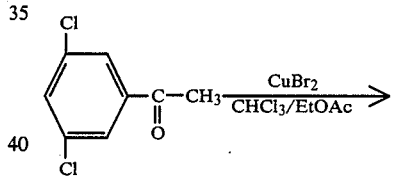

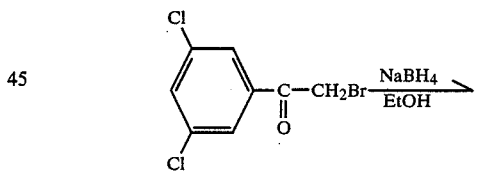

Alternatively, a formula (I) compound wherein Y is hydrogen may be prepared from the corresponding formula (I) compound wherein Y is amino, via a deamination reaction, by dissolving the amine in 50-52% aqueous hypophosphorous acid ($H_3PO_2$). The solution is chilled below 10° C., and an equimolar or excess amount of sodium nitrite is added to an aqueous solution with stirring over a period of time. On completion of the addition, the reaction mixture is warmed to room temperature and stirred for an additional period of time. The product is then recovered from the reaction mixture by standard laboratory procedures and purified if so desired.

The preparation of 4-substituted aminoacetophenones required for the preparation of 4-substituted phenylethane derivatives which are now found to be useful for raising meat-producing animals, is exemplified as follows:

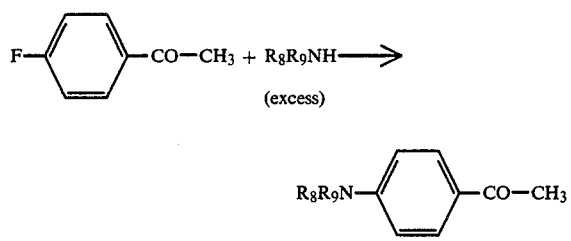

The fluorine displacement is carried out with excess amine in the presence or absence of a solvent; and, if a solvent is required, water appears to be the most useful. With volatile amines, the reaction is conducted in a sealed vessel and generally temperatures of 50°–100° C. are sufficient to complete the reaction.

Chlorination and bromination of these aminoacetophenones may be conducted with N-chlorosuccinimide and N-bromosuccinimide in toluene, chlorobenzene or dichlorobenzene at 90°–100° C. Iodination may be conducted with NaI/N,N-dichlorobenzenesulfonamide or iodine monochloride in acetic acid.

By reacting these acetophenones with bromine in chloroform or methylene chloride, the corresponding phenacyl bromides are prepared. These phenacyl bromides are then reacted with $R_2R_3N$ amines and the aminoketones are reduced with $NaBH_4$ or $NaCNBH_3$ by conventional techniques described in references cited hereinbefore. Naturally, compounds which contain groups reactive to halogen, such as when $R_8$ is alkenyl, require other approaches that are discussed below.

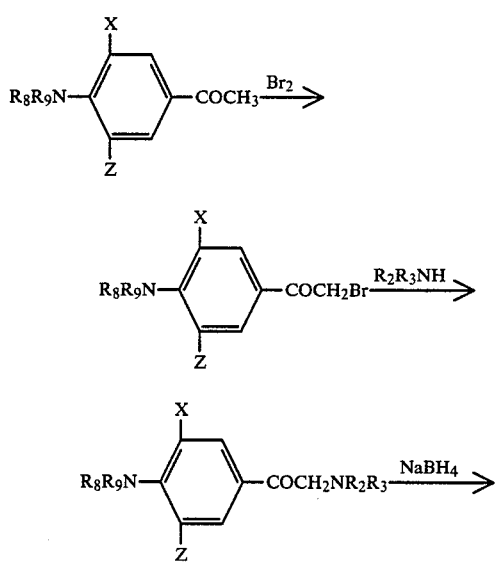

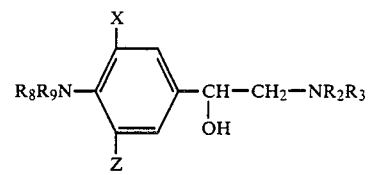

wherein X and Z are hydrogen, chlorine, or bromine and $R_2$ and $R_3$ are hydrogen, $C_1$–$C_4$ alkyl, or $C_{2-3}$ alkenyl groups.

The compounds of formula I, wherein $R_8$ and $R_9$ are groups other than both being hydrogen are also prepared by the following general scheme:

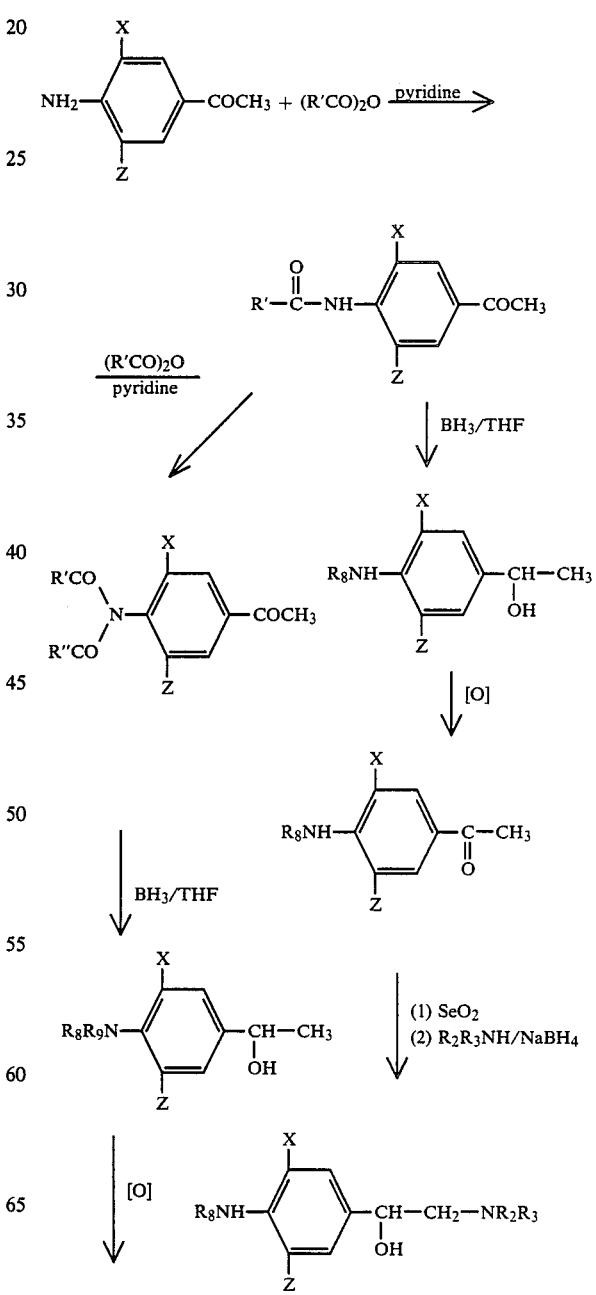

-continued

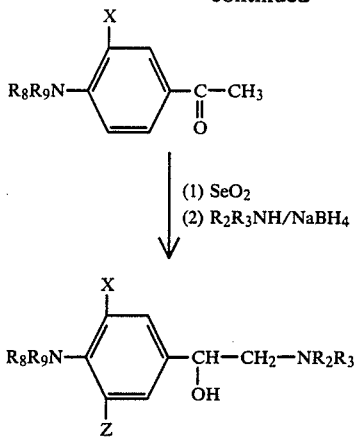

The methods utilized in the above scheme are either reported in references cited hereinbefore or by conventional methods. Oxidation of the alcohol may be conducted with chromic acid (Jones Reagent), MnO$_2$, pyridinium chlorochromate, or other oxidizing agents. Where X or Z are the BH$_3$-reducible groups, CN, COOR, or CONH$_2$, the appropriate acetophenones are prepared by displacement of X or Z represented by bromine with CuCN/DMF at 100°–160° C. by the conventional method, after reduction of the acylated aminoacetophenones in the first step followed by re-oxidation in the second step of the above procedure. The cyano substituted-amino-acetophenones are then converted to their corresponding ethanolamines, which are then converted to the desired esters, acids, and amides by conventional methods, such as R$_1$OH/acid→esters, hydrolyses→acids and partial hydrolyses→amides.

Furthermore, compounds of the following structure are prepared by allowing the corresponding ethanolamines to react with an equivalent or slight excess of the acid anhydrides with or without organic bases such as tertiary amines or pyridine. The reactions are conducted in inert solvents

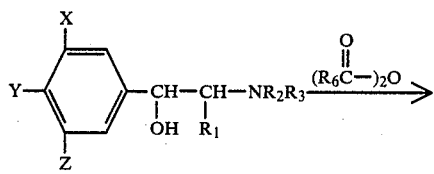

such as chlorinated hydrocarbons, or aromatic solvents at 0°–25° C. Reaction of the anhydride at the hydroxyl group proceeds well provided R$_2$ and R$_3$ are groups other than hydrogen and when R$_2$ is hydrogen, R$_3$ is a substituent containing a tertiary carbon attached to nitrogen.

Compounds of the following structure which contain alkanoyl or aroyl groups on ethanolamine moiety are readily prepared by using two equivalents or more of the acid anhydrides in the presence of a tertiary amine, such as triethylamine, or pyridine in an inert solvent (CH$_2$Cl$_2$, CHCl$_3$, toluene, etc.) at 50°–100° C.

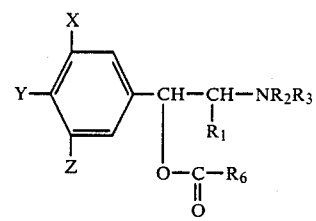

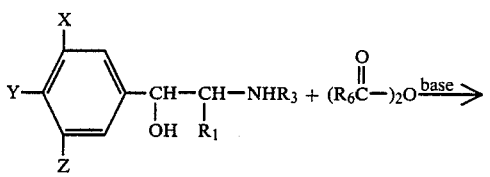

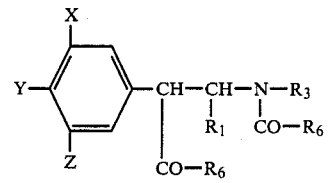

Additionally, Formula I compounds, wherein R$_8$ and R$_9$ are selected from hydrogen and C$_3$–C$_4$ alkenyl, are prepared by alkenylation of 4-amino-3,5-disubsituted phenacyl bromides in dimethylformamide (DMF) in the presence of an acid acceptor, such as triethylamine or sodium carbonate, at 70°–100° C. to afford mono- and dialkenylated products which are separated and converted to I by conventional methods. The following scheme illustrates above-described general method:

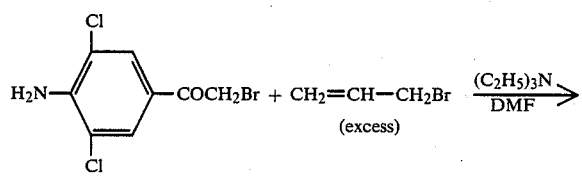

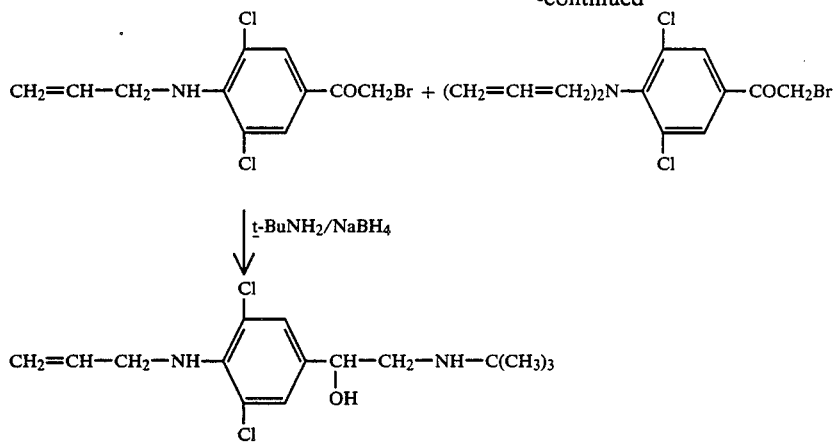

Formula (I) compounds wherein $R_4$ is $OR_6$ and $SR_{11}$, wherein $R_6$ and $R_{11}$ are as hereinabove defined, may be prepared by converting the alcohol ($R_4$=OH) with thionyl chloride under an inert blanket of gas such as nitrogen at a temperature range of from about 0° to 10° C. and preferably at 0° to 5° C. for a reaction period sufficient to essentially complete the reaction. The thus obtained halo compound is isolated by conventional methods and is then reacted with the appropriate alcohol or mercaptan, under an inert blanket of gas, such as nitrogen at a temperature range of from about 0° to 50° C. The formula (I) product thus obtained is then isolated by standard laboratory methods and purified, if so desired. The above reaction sequence may be graphically illustrated as follows:

formula (I) compound wherein $R_4$ is OH in the corresponding $R_6OH$ alcohol and saturating the thus obtained solution with dry HCL gas. The reaction mixture is then stirred at room temperature for a period of time sufficient to essentially complete the reaction and the product is then isolated by standard laboratory procedures and purified, if so desired. This reaction sequence may be illustrated as follows:

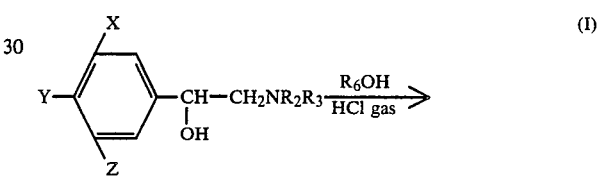

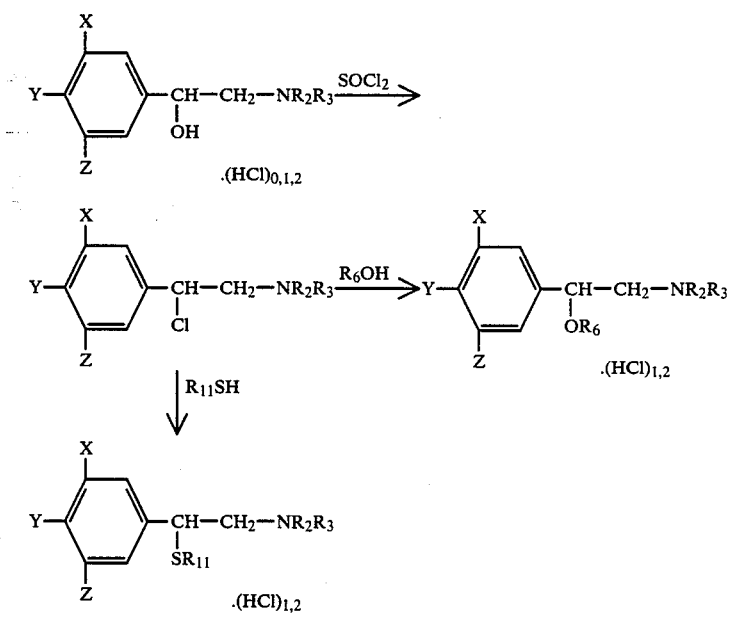

wherein X, Y, Z, $R_2$, $R_3$, $R_6$ and $R_{11}$ are as hereinabove defined.

These displacement reactions may also be performed by using an excess of alkoxide ($R_6O^-$) or mercaptide ($R_{11}S^-$) in an inert solvent such as tetrahydrofuran to afford the above ethers and thioethers in a similar manner.

Alternatively, a formula (I) compound wherein $R_4$ is $OR_6$ may be prepared by dissolving the corresponding -continued

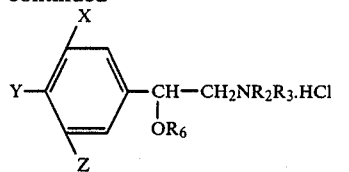

wherein X, Y, Z, $R_2$, $R_3$ and $R_6$ are as hereinabove defined.

In the present specification and claims, the term α,α-dimethylphenethyl means a structure having the following configuration:

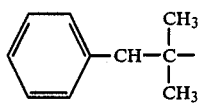

When orally administered in the feed, generally about 0.01 to 300 grams per ton of feed of the above-identified phenylethane derivative or acid addition salt thereof, is effective for enhancing the growth rate and improving the efficiency of feed utilization by the above-mentioned meat-producing animals.

Since the effective and preferred dietary levels of the active ingredient vary somewhat from species to species in the above-mentioned animals, said levels for each animal species are listed in Table I below on a gram per ton of feed basis:

TABLE I

| Compound | Effective Feed Level g/Ton | Preferred Level g/Ton | Animal |
|---|---|---|---|
| Formula (I) | 0.1–200 | 1–100 | Sheep, Goats |
| | 0.01–50 | 0.1–10 | Chickens, Rabbits |
| | 0.01–50 | 0.1–10 | Turkeys |
| | 0.1–300 | 1–100 | Cattle |

Animal feed compositions which will provide the desired growth promotion and feed efficiency in the above-mentioned animals can be prepared by admixing the phenylethane derivative or acid addition salt thereof, or an animal feed supplement containing said compound, with a sufficient quantity of an appropriate animal feed to provide the desired level of active compound in said feed.

Animal feed supplements can be prepared by admixing about 10% to 75% by weight of the phenylethane derivative of acid addition salt thereof, with about 90% to 25% by weight of a suitable carrier or diluent. Carriers suitable for use to make up the feed supplement compositions include the following: alfalfa meal, soybean meal, cottonseed oil meal, linseed oil meal sodium chloride, cornmeal can molasses, urea, bone meal, corn-cob meal and the like. The carrier promotes a uniform distribution of the active ingredient in the finished feed into which the supplement is blended. It thus performs an important function by ensuring proper distribution of the active ingredient throughout the feed.

If the supplement is used as a top dressing for feed, it likewise helps to ensure uniformity of distribution of the active material across the top of the dressed feed.

For parenteral administration, the phenylethane derivative may be prepared in the form of a paste or pellet and administered as an implant, usually under the skin of the head or ear of the animal in which enhanced growth rate and/or improved efficiency of feed utilization is sought.

In practice, parenteral administration generally involves injection of a sufficient amount of the abovesaid phenylethane derivative to provide the animal with from 0.001 to 50 mg/kg of body weight of the active ingredient. The preferred dosage level for cattle is the range of from 0.001 to 25 mg/kg of body weight of the active phenylethane derivative. The preferred dose level of said phenylethane derivative for poultry is about 0.001 to 35 mg/kg of animal body weight and the preferred dose level of said phenylethane derivative for sheep and goats is 0.001 to 40 mg/kg of animal body weight. The preferred dose level for rabbits in 0.001 to 35 mg/kg of animal body weight.

Paste formulations can be prepared by dispersing the actie phenylethane derivative in a pharmaceutically acceptable oil such as peanut oil, sesame oil, corn oil or the like.

Pellets containing an effective level of the phenylethane derivative can be prepared by admixing the above-said active ingredient with a diluent such as carbowax, biodegradable polymers, carnauba wax, or the like. A lubricant, such as magnesium stearate or calcium stearate may be added to improve the pelleting process if desired.

It is, of course, recognized that more than one pellet may be administered to an animal to achieve the desired dose level which will provide the increased growth rate and/or improve efficiency of feed utilization by said animal. Moreover, it has been found that additional implants may also be introducted periodically during the treatment period in order to maintain the proper drug release rate in the animal's body.

In addition to enhanced growth promotion and improved efficiency of feed utilization by meatproducing animals, the compounds of the present invention have the added advantage that, at selected levels of administration, they increase the deposition of lean meat (i.e., muscle or protein) in said animals and improve the carcass quality thereof by increasing the ratio of lean meat to fat in the animals receiving them. This biological response has substantial advantage to poultrymen, cattlemen, and swine, sheep and goat producers since administration of said compounds at selected levels yields leaner animals which command premium prices from the meat industry.

These and other advantages of the present invention will become apparent from the examples set forth below. Such examples are provided only by way of exemplification and are not intended to be expressions of limitations on the invention.

EXAMPLE 1

Evaluation of Test Compounds as Animal Growth Promoters

CFI female mice from Carworth Farms are received when they are six weeks old. They are housed ten to a cage in air-conditioned rooms (72° F. to 76° F.) with automatically controlled lights, 14 hours on and 10 hours off. The basal diet used in these studies is Purina Laboratory Chow (see description below), which is supplied ad libitum. Water is allowed ad libitum.

Thirteen days after arrival, the mice are weighed in groups of ten and assigned at random to the different treatments. The concentration of the different compounds in the diet is indicated in the following tables.

Twelve days later the mice are weighed again, and the experiment terminated. Test data are provided in Table II below wherein data are reported as percentage gain over controls. The following is description of the diet to which the growth-promoting compounds were added.

| DIET<br>Guaranteed Analysis | |
|---|---|
| Crude protein not less than | 23.0% |
| Crude fat not less than | 4.5% |
| Crude fiber not more than | 6.0% |
| Ash not more than | 9.0% |

Ingredients

Meat and bone meal, dried skimmed milk, wheat germ meal, fish meal, animal liver meal, dried beet pulp, ground extruded corn, ground oat groats, soybean meal, dehydrated alfalfa meal, cane molasses, animal fat preserved with BHA, vitamine $B_{12}$ supplement, calcium pantothenate, choline chloride, folic acid, riboflavin supplement, brewer's dried yeast, thiamin, niacin, vitamin A supplement, D-activated plant sterol, vitamin E supplement, calcium carbonate, dicalcium phosphate, iodized salt, ferric ammonium citrate, iron oxide, manganous oxide, cobalt carbonate, copper oxide, zinc oxide.

TABLE II

Evaluation of Test Compounds as Animal Growth Promoters

| Dosage | Initial Mouse Wt. (g) | Final Mouse Wt. (g) | Gain (grams) | % Gain Over Control |
|---|---|---|---|---|
| 4-Amino-α-(tert-butyl-aminomethyl)-3,5-dichlorobenzyl alcohol hydrochloride (ppm in diet) | | | | |
| 0 | 23.46 | 24.67 | 1.21 | |
| | 23.46 | 24.49 | 1.03 | |
| | 22.79 | 24.62 | 1.83 | |
| | 24.10 | 58.98 | 1.88 | |
| | 24.23 | 25.52 | 1.29 | |
| | 23.63 | 24.93 | 1.30 | |
| | 23.33 | 24.76 | 1.43 | |
| | 22.75 | 23.86 | 1.11 | |
| Control Average | 23.47 | 24.85 | 1.39 | — |
| 50 | 22.95 | 25.63 | 2.68 | |
| | 23.91 | 26.14 | 2.23 | |
| | 24.26 | 26.30 | 2.04 | |
| Average | 23.71 | 26.02 | 2.32 | +66.9 |
| 100 | 23.50 | 25.39 | 1.89 | |
| | 23.80 | 26.04 | 2.24 | |
| | 23.00 | 25.65 | 2.65 | |
| Average | 23.43 | 25.69 | 2.26 | +62.6 |
| 200 | 23.03 | 24.80 | 1.77 | |
| | 24.50 | 26.12 | 1.62 | |
| | 23.08 | 25.04 | 1.96 | |
| Average | 23.54 | 25.32 | 1.78 | +28.1 |

The procedure described above is repeated for the evaluation of each of the following compounds using different control animals for each test. Twelve days after the tests are started, the animals are weighed and the test terminated. The results of each test are reported in Table III below as weight gains for each test group and percent gain for each test group over the weight gains obtained by the control animals in the specific test in which the compound is evaluated.

TABLE III

Evaluation of Test Compounds as Animal Growth Promoters

| Compound | Dosage (ppm) | Gain (grams) | % Gain Over Controls |
|---|---|---|---|
| 4-Amino-3,5-dibromo-α-[(tert-butylamino)methyl]-benzyl alcohol hydrochloride | 400 | 16.5 | +22.2 |
| | 200 | 20.4 | +51.1 |
| | 100 | 22.9 | +69.0 |
| | 50 | 23.3 | +72.6 |
| 4-Amino-3,5-dibromo-α-[(diisopropylamino)methyl]-benzyl alcohol hydrochloride | 200 | 20.2 | +46.4 |
| | 100 | 16.9 | +22.5 |
| 4-amino-α-[(dimethylamino)methyl]benzyl alcohol | 200 | 17.6 | +28.3 |
| | 100 | 15.6 | +13.0 |
| 4'-amino-α-[(diisopropylamino)methyl]benzyl alcohol hydrochloride | 200 | 16.5 | +18.7 |
| | 100 | 14.2 | +2.2 |
| 4-Amino-3,5-dichloro-α-[(dimethylamino)methyl]benzyl alcohol hydrochloride | 100 | 18.4 | +7.6 |
| 4-Amino-3,5-dichloro-α-[(diisopropylamino)methyl]-benzyl alcohol hydrochloride | 200 | 23.9 | +66.0 |
| | 100 | 21.3 | +47.9 |
| 4-Amino-3,5-dichloro-α-[(cyclohexylamino)methyl]-benzyl alcohol hydrochloride | 200 | 19.3 | +48.5 |
| | 100 | 16.3 | +25.4 |
| 4-amino-α-[(tert-butylamino)methyl]benzyl alcohol | 200 | 19.6 | +88.5 |
| | 100 | 18.2 | +75.0 |
| | 50 | 17.9 | +72.1 |
| | 25 | 13.6 | +30.8 |
| 4-Amino-3,5-dichloro-α-[(methylamino)methyl]benzyl alcohol hydrochloride | 200 | 15.6 | +54.5 |
| | 100 | 18.9 | +87.1 |
| 4-amino-α-[(methylamino)methyl]benzyl alcohol hydrochloride | 100 | 14.8 | +18.4 |
| α-(4-Amino-3,5-dichlorophenyl)-4-morpholineethanol hydrochloride | 200 | 15.9 | +34.7 |
| | 100 | 14.0 | +18.6 |
| 4-Amino-α-[(sec-butylamino)methyl]-3,5-dichloro-benzyl alcohol | 200 | 13.2 | +16.8 |
| 4-Amino-3,5-dichloro-α-[(-3-methoxypropyl)amino]-methyl benzyl alcohol | 200 | 15.4 | +23.2 |
| | 100 | 23.0 | +84.0 |
| 4-Amino-3,5-dichloro-α-[(diallylamino)methyl]benzyl alcohol hydrochloride | 200 | 17.4 | +39.2 |
| | 100 | 18.4 | +47.2 |
| 4-Amino-3,5-dichloro-α-[(benzylamino)methyl]benzyl | 200 | 10.6 | +19.1 |

TABLE III-continued
Evaluation of Test Compounds as Animal Growth Promoters

| Compound | Dosage (ppm) | Gain (grams) | % Gain Over Controls |
|---|---|---|---|
| alcohol hydrochloride | | | |
| 4-Amino-α-[(butylamino)methyl]-3,5-dichlorobenzyl alcohol | 100 | 14.6 | +64.0 |
| 4-Amino-3,5-dichloro-α-[(4-methyl-1-piperazinyl)methyl]benzyl alcohol | 200 | 9.4 | +5.6 |
| | 100 | 9.5 | +6.7 |
| 4-Amino-3,5-dichloro-α-[(isopropylamino)methyl]benzyl alcohol | 200 | 13.1 | +26.0 |
| | 100 | 18.9 | +81.7 |
| 4-Amino-α-(aminomethyl)-3,5-dichlorobenzyl alcohol hydrochloride | 100 | 13.4 | +19.0 |
| 4-Amino-3,5-dichloro-α-[(hexylamino)methyl]benzyl alcohol | 200 | 16.8 | +15.9 |
| | 100 | 19.2 | +32.8 |
| α-[(tert-butylamino)methyl]-3,5-dichlorobenzyl alcohol hydrochloride | 200 | 19.3 | +33.1 |
| | 100 | 20.2 | +39.3 |
| 4-Amino-3,5-dichloro-α-[(diethylamino)methyl]benzyl alcohol hydrochloride | 100 | 17.5 | +20.7 |
| α-[(allylamino)methyl]-4-amino-3,5-dichlorobenzyl alcohol | 200 | 16.8 | +118.2 |
| | 100 | 17.1 | +122.1 |
| 4-Amino-α-(anilinomethyl)-3,5-dichlorobenzyl alcohol | 200 | 20.7 | +25.5 |
| | 100 | 17.5 | +6.1 |
| 4-Amino-α-[1-tert-butylamino)ethyl]-3,5-dichlorobenzyl alcohol hydrochloride | 200 | 22.7 | +37.6 |
| | 100 | 23.8 | +44.5 |
| 4-Amino-3-bromo-α-[(tert-butylamino)methyl]-5-chlorobenzyl alcohol hydrochloride | 200 | 18.5 | +60.9 |
| | 100 | 19.5 | +69.6 |
| α-[(tert-butylamino)methyl]-m-hydroxybenzyl alcohol hydrochloride | 200 | 15.8 | +9.0 |
| | 100 | 19.9 | +37.2 |
| α-[(isopropylamino)methyl]-m-hydroxybenzyl alcohol hydrochloride | *400 | — | +54.4 |
| | 200 | — | +53.0 |
| | 100 | — | +39.7 |
| α-[(Amino)methyl-m-hydroxybenzyl alcohol hydrochloride | 200 | — | +4.4 |
| | 100 | — | +30.7 |
| 4-Amino-N—tert-butyl-3,5-dichloro-β-methoxyphenethyl hydrochloride | 200 | 18.8 | +37.2 |
| | 50 | 21.6 | +57.7 |
| 4'-[2-(tert-butylamino)-1-hydroxyethyl]-2'-chloroacetanilide | 200 | 16.8 | +107.9 |
| | 100 | 18.4 | +127.7 |
| 4-Amino-α-[(tert-butylamino)methyl]-3,5-diiodobenzyl alcohol hydrochloride | 200 | 21.1 | +27.1 |
| | 100 | 20.0 | +20.5 |
| 4-Amino-N—tert-butyl-3,5-dichlorophenethylamine hydrochloride | 50 | 12.3 | 7.9 |
| α-(Aminomethyl)-m-chlorobenzyl alcohol hydrochloride | 200 | 15.8 | +4.6 |
| α-[(Tert-butylamino)methyl]-3,5-dichloro-4-dimethylaminobenzyl alcohol | 200 | 16.0 | 0 |
| | 50 | 21.9 | +36.9 |
| 4-Amino-3,5-dichloro-α-{[(3-phenylpropyl)amino]methyl}benzyl alcohol | 200 | 16.9 | +5.6 |
| | 50 | 18.9 | +18.1 |
| α-[(Tert-butylamino)methyl]-3,5-dichloro-4-methylaminobenzyl alcohol | 200 | 19.4 | +21.3 |
| | 50 | 24.4 | +52.5 |
| 4-Amino-N—tert-butyl-3,5-dichloro-β-isopropoxyphenethylamine | 200 | 14.8 | −7.5 |
| | 50 | 20.9 | +30.6 |
| 4-Amino-N—tert-butyl-3,5-dichloro-β-ethoxyphenethylamine hydrochloride | 200 | 15.9 | +30.3 |
| | 50 | 22.8 | +86.9 |
| Methyl-p-{3-[(4-amino-3,5-dichloro--hydroxyphenethyl)amino]propyl}benzoate | 200 | 24.3 | +22.6 |
| | 50 | 19.0 | −4.1 |
| Methyl-4-[2-(tert-butylamino)-1-hydroxyethyl]-2,6-dichlorocarbanilate | 50 | 27.9 | +40.8 |
| 4'-[2-(Tert-butylamino)-1-hydroxyethyl]-2',6'-dichloroacetanilide hydrochloride | 200 | 21.8 | +37.1 |
| | 50 | 23.4 | +47.2 |
| 5-[2-(Tert-butylamino)-1-hydroxyethyl]-3-chloroanthranilonitrile | 200 | 27.3 | +90.9 |
| | 50 | 26.2 | +83.2 |
| 4-Amino-β-(benzyloxy)-N—tert-butyl-3,5-dichlorophenethylamine hydrochloride | 200 | 22.6 | +58.0 |
| | 50 | 22.4 | +56.6 |
| α-[(Tert-butylamino)methyl]-3,5-dichloro-4-isopropylaminobenzyl alcohol | 200 | 24.6 | +72.0 |
| | 50 | 24.3 | +69.9 |
| | 12 | 28.0 | +95.8 |
| | 3 | 27.3 | +90.8 |
| 5-[2-(Tert-butylamino)-1-hydroxyethyl]-anthranilonitrile | 200 | 29.6 | +79.4 |
| | 50 | 29.9 | +81.2 |
| Methyl-5-[2-(tert-butylamino)-1-hydroxyethyl]-3-chloroanthranilate hydrochloride | 200 | 24.4 | +47.9 |
| | 50 | 20.1 | +21.8 |
| 4'-[2-Tert-butylamino)-1-hydroxyethyl]-2',6'-dichlorovaleranilide | 200 | 26.1 | +58.2 |
| | 50 | 26.4 | +60.0 |
| Benzyl-4-[2-(tert-butylamino)-1-hydroxyethyl]-2,6-dichlorocarbanilate | 50 | 25.1 | +52.1 |
| 4-Amino-N—tert-butylamino-3,5-dichloro-β-(methylthio)phenethylamine hydrochloride | 200 | 25.4 | +55.8 |
| | 50 | 25.3 | +55.2 |
| N—Tert-butyl-3,5-dichloro-β-methoxyphenethylamine hydrochloride | 200 | 21.5 | +50.3 |
| | 50 | 25.8 | +80.4 |

EXAMPLE 2

Evaluation of Test Compounds as Animal Growth Promoters

The procedure of Example 1 is used in this evaluation. The diet is the same as described in said example and data obtained are reported as percent gain over controls. Data are reported in Table IV below.

TABLE IV
Evaluation of Test Compounds as Animal Growth Promoters

| | Initial | Final | Gain | % Gain Over Control |
|---|---|---|---|---|
| Dosage | Wt. (g) | Wt. (g) | (grams) | |
| 4-Amino-α-(tert-butylaminomethyl)-3,5-dichlorobenzyl alcohol hydrochloride (ppm in diet) | | | | |
| 0 | 24.49 | 25.17 | 6.8 | |
| | 24.25 | 26.06 | 1.81 | |
| | 23.65 | 25.43 | 1.78 | |
| | 22.83 | 24.33 | 1.50 | |
| | 24.39 | 25.59 | 1.20 | |
| | 24.36 | 26.06 | 1.70 | |
| | 23.11 | 24.50 | 1.39 | |
| | 23.54 | 24.82 | 1.28 | |
| Average | 23.83 | 25.25 | 1.42 | — |
| 200 | 23.46 | 25.49 | 2.03 | |
| | 23.68 | 25.97 | 2.37 | |
| | 23.56 | 25.40 | 1.84 | |
| Average | 23.57 | 25.62 | 2.05 | +44.4 |

EXAMPLE 3

Evaluation of test compounds as antilipogenic agents and animal growth promoting agents The procedure of Example 1 is repeated excepting that three cages of 10 mice are used for each treatment level and after the final weights have been taken, all mice are necropsied and the percent body fat for each treatment group determined. The method for determining percent body fat of the animals is hereinafter described. Data obtained are reported in Table V below.

A. Preparation of carcasses:

Stomach and intestines are removed from each mouse. All other viscera, including skin and fur, remaining intact. Each cage of mice (10) is weighed and autoclaved at 120° C. (15 psi) for 30 minutes. Carcasses from each cage are then homogenized. The homogenate is weighed and duplicate 5-gram samples are removed for analysis.

B. Fat analysis:

Fifteen mililiters of concentrated hydrochloric acid is added to each 5-gram sample and mixed well. Samples are heated in an 84° C. water bath for 2 hours and then removed. Thirty ml of petroleum ether is added to each sample, 15 ml at a time and mixed well on a vortex mixer. Aqueous and organic phases are separated by low speed centrifugation and the ether layer (containing fat) is extracted into tared 30 ml beakers. Beakers are let to dry overnight and the beaker containing fat is reweighed to determine grams of fat per five grams of homogenate. Total body fat in the carcass is calculated as follows:

$$\% \text{ fat} = \frac{\left[\begin{array}{c}\text{grams fat} \\ \text{in sample}\end{array}\right]\left[\begin{array}{c}\text{grams total} \\ \text{homogenate}\end{array}\right]}{\left[\begin{array}{c}\text{gram weight} \\ \text{of sample}\end{array}\right]\left[\begin{array}{c}\text{carcass weight} \\ \text{of mice (g)}\end{array}\right]} \times 100$$

TABLE V
Antilipogenic Agent Evaluation and Growth Enhancement Evaluation in Mice

| Compound | Level in Diet (ppm) | Number of Mice per Treatment | Average Initial Weight (g) | Average Final Weight (g) | Gain per Mouse (g) | % Body Fat | Change in % Fat from Control |
|---|---|---|---|---|---|---|---|
| H$_2$N—[ring with Cl, Cl, OH, CH—CH$_2$—NH—C(CH$_3$)$_3$] | 0 | 50 | 23.6 | 25.0 | 1.4 | 11.95 | — |
| | 50 | 30 | 23.7 | 26.0 | 2.3 | 11.95 | 0 |
| | 100 | 30 | 23.4 | 25.7 | 2.3 | 10.23 | −14.40 |
| | 200 | 30 | 23.5 | 25.3 | 1.8 | 10.50 | −12.13 |
| | 400 | 30 | 23.4 | 24.9 | 1.4 | 9.10 | −23.80 |

EXAMPLE 4

Evaluation of test compounds as animal feed additives for the enhancement of the growth rate of poultry One day old Hubbard X Hubbard Crossbred Chicks, randomly allotted to pens of ten chicks (5 males and 5 females) each.

Eight pens of chicks are used for unmedicated controls, and four pens of chicks are used at each level of drug. The duration of the experiment is 28 days.

The controls are offered an unmedicated diet of Broiler Ration No. 453 (composition given below) and water ad libitum. Medicated chicks are offered the same diet containing the test drug at the levels indicated above, and water ad libitum. The weight of the chicks is determined at the beginning and on completion of the experiments. Weight gains and the amount of feed consumed are also determined. The thus obtained data are averaged and summarized in Table VI below, wherein the percent improvement in weight gains and feed/gain ratios are given.

| Component | Percent by Weight | |
|---|---|---|
| Ground yellow corn | 53.45 | |
| Soybean oil meal (49%) | 28.00 | |
| Menhaden fish meal (60%) | 5.0 | |
| Corn gluten meal (60%) | 5.00 | |
| Dehydrated alfalfa meal (17%) | 2.00 | |
| Stabilized fat | 4.00 | |
| Dicalcium phosphate | 1.20 | |
| Ground limestone | 0.50 | |
| Sodium chloride | 0.30 | |
| Trace minerals mixture* | 0.05 | |
| Vitamin premix** | 0.50 | |
| | 100.00 | |
| *Trace Mineral Mixture | 1 lb/ton furnishes | |
| Manganese | 12.50% | 62.5 ppm |
| Iron | 6.00 | 30.0 |
| Zinc | 5.00 | 25.0 |
| Copper | 0.65 | 3.25 |
| Iodine | 0.35 | 1.75 |
| Cobalt | 0.25 | 1.25 |
| Calcium minimum | 15.30 | |

-continued

| Calcium maximum | 17.35 | |
| --- | --- | --- |
| **Vitamin Premix for 1-ton | | Weight in Gram |
| DL Methionine | | 453.6 |
| BHT (butylated hydroxy toluene) | | 113.6 |
| Vitamin A (30,000 mcg/g) | | 100.0 |
| Vitamin D$_3$ (200,000 mcg/g) | | 5.0 |
| Vitamin E (20,000 mcg/lb) | | 45.4 |
| Riboflavin | | 4.0 |
| Niacinamide | | 25.0 |

TABLE VI

Mean Weight Gain and Feed Efficiency of Control and Test Compound - Treated Chicks
Thirteen-Day Battery Testing

| Treatment | ppm in Diet | Mean Gain (g) | % Control | F/G | % Improvement over Control |
| --- | --- | --- | --- | --- | --- |
| Control | 0 | 266.5 | — | 1.40 | — |
| 4-Amino-α-[(tert-butylamino)methyl] | 0.3 | 271.8 | +2.0 | 1.40 | 0 |
| 3,5-dichlorobenzyl alcohol | 0.6 | 274.3 | +2.9 | 1.38 | +1.4 |
| | 1.25 | 259.9 | −2.5 | 1.41 | −0.7 |
| | 2.5 | 260.8 | −2.1 | 1.39 | +0.7 |
| | 5.0 | 251.9 | −5.5 | 1.40 | 0 |
| 4-Amino-3,5-dibromo-α-[(tert-butyl- | 0.3 | 270.8 | +1.6 | 1.40 | 0 |
| amino)methyl]benzyl alcohol hydrochloride | 0.6 | 271.8 | +2.0 | 1.38 | +1.4 |
| | 1.25 | 267.5 | +0.4 | 1.39 | +0.7 |
| | 2.5 | 265.2 | −0.5 | 1.38 | +1.4 |
| | 5.0 | 270.3 | +1.4 | 1.37 | +2.1 |

EXAMPLE 5

Evaluation of test compounds as animal feed additives for the enhancement of growth rate and improvement in feed efficiency of mice.

Four-week old female outbred rats (5-gram range) from Charles River Breeding Laboratories, 251 Ballardvale Street, Wilmington, Mass. 01887, are housed 2/cage in air-conditioned rooms (72° F. to 76° F.) with automatically controlled lights, 14 hours on and 10 hours off. The basal diet used in these studies is Purina Laboratory Chow which is supplied ad libitum. Water is also given ad libitum.

Four days after arrival, the animals are weighed and allotted to treatment groups to minimize weight variation. Ten rats are used per treatment group. Drugs are administered in the feed at 2 ppm, 10 ppm and 50 ppm for a period of 12.5 weeks. Animals are weighed weekly and feed consumption corrected for spillage recorded daily. The results of this trial are shown below in Table VII.

EXAMPLE 6

Evaluation of test compounds as animal feed additives for (1) the enhancement of the growth rate of poultry, (2) improvement in feed utilization thereby, (3) increase in the deposition of muscle tissue or protein in said birds and (4) improvement in the carcass quality of treated birds The procedure of Example 4 is employed in the following tests, excepting that eight pens of chicks are used for each treatment level, and the drug is administered in the chick diet for three weeks, i.e., from the start of week five through week seven. The experiment is terminated when the birds are seven weeks old. The weight of the chicks is determined at the beginning and on completion of the experiment, and the weight gains and the amount of feed comsumed calculated. In addition, 10 males and 10 females from each group are randomly selected and sacrificed by decapitation. These birds were bled, and the feathers and feet removed. The defeathered carcass, with visera intact, were ground. Samples of the ground carcasses were then analyzed for protein, fat and moisture content. The results of these tests are reported in Table VIII below where it can be seen that chicks receiving from 0.25 to 4.0 ppm of the test compound showed an increase in growth rate, improvement in utilization of their feed, increased deposition of muscle tissue or protein and improved overall carcass quality.

Moisture was determined by placing 10 gram samples in aluminum foil pans, and the weights of sample and pan recorded. These samples were dried overnight in a forced air oven, and the dry weight of the pan and sample recorded.

Protein content was determined by a Macro Kjeldahl method, using 1 gram samples of the ground samples.

TABLE VII

Evaluation of Test Compounds as Animal Feed Additives for the Enhancement of Growth Rate
and Improvement in Feed Efficiency - Mice

| Treatment | Dose ppm | Gain[a] (g) | Feed Consumption[b] (g) | Feed/Gain % Improvement |
| --- | --- | --- | --- | --- |
| Control | | 157 | 1304 | 8.31 |
| 4-Amino-α-(tert-butylaminomethyl)-3,5-dichloro- | 2 | 178 (+13.4%) | 1443 (+10.7%) | 8.11 (+2.4%) |
| benzyl alcohol hydrochloride | 10 | 186 (+18.5%) | 1467 (+11.5%) | 7.89 (+5.1%) |
| | 50 | 175 (+11.5%) | 1394 (+6.9%) | 7.97 (+4.1%) |
| 4-Amino-3,5-dibromo-α-[(tert-butylamino)methyl]- | 2 | 164 (+4.5%) | 1362 (+4.5%) | 8.3 (0.1%) |
| benzyl alcohol hydrochloride | 10 | 185 (+7.8%) | 1459 (+11.9%) | 7.89 (+5.1%) |
| | 50 | 184 (+17.2%) | 1416 (+8.6%) | 7.70 (+7.3 |

[a]Values given are the total average gain (g) per rat for the entire experimental period.
[b]Values given are the total average feed consumed per rat for the entire experimental period.
Figures in parentheses are % improvement over control.

Fat was determined by digesting 5 gram samples of the ground birds in 50 ml plastic centrifuge tubes and digesting the samples with 5 ml of concentrated hydrochloric acid at 80° C. for 120 minutes. The digested samples were treated with 15 ml of petroleum ether, mixed and centrifuged at 1500 rpm for 10 minutes, and the ether layer separated from the solids. The sample was extracted again in the same manner, and the ether layers mixed. The ether was then evaporated, and the remaining residue weighed to determine the amount of fat in the sample.

TABLE VIII

Evaluation of Test Compound for Increasing the Growth Rate of Poultry, Improving Efficiency of Feed Utilization Thereby, Enhancing the Deposition of Muscle Tissue or Protein Thereof and Improving the Carcass Quality of Said Poultry

| Av/bird | Compound 4-Amino-α-[(tert-butylamino)methyl]-3,5-dichlorobenzyl alcohol (ppm) in diet | | | | | |
|---|---|---|---|---|---|---|
| | 0 | 0.25 | 0.50 | 1.0 | 2.0 | 4.0 |
| Gain (kg) | 1.08 | 1.12 | 1.12 | 1.12 | 1.11 | 1.10 |
| % + control | | +3.7 | +3.7 | +3.7 | +2.8 | +1.8 |
| Feed consumed (kg) | 2.35 | 2.39 | 2.36 | 2.37 | 2.35 | 2.36 |
| % ± control | | +1.7 | +0.4 | +0.9 | 0 | +0.4 |
| FE | 2.21 | 2.14 | 2.13 | 2.13 | 2.13 | 2.15 |
| % + control | | +3.2 | +3.6 | +3.6 | +3.6 | +2.7 |
| % protein ± control: | | | | | | |
| females | | +5.7 | +4.5 | +5.6 | +5.5 | +6.2 |
| males | | +2.5 | +5.9 | +3.2 | +4.3 | +2.3 |
| % fat ± control: | | | | | | |
| females | | −9.0 | −10.0 | −8.5 | −11.5 | −9.0 |
| males | | −8.4 | −8.8 | −14.2 | −13.7 | −10.5 |

EXAMPLE 7

Growth Enhancement, Feed Efficiency Improvement, Increased Deposition of Muscle Tissue and/or Protein and Improvement in Carcass Composition To determine the effect of feeding experimental compounds to ruminants, wether lambs are randomly allotted to pens in groups of four. Five replications per treatment are used. The sheep are weighed and permitted feed and water ad libitum. The feed is weighed daily, and uneaten feed from the previous day is collected and weighed. Test lambs receive the same diet as control animals, but with the addition of experimental compound at a concentration of from 1 to 100 ppm. The tests are conducted for a period of eight weeks at the end of which the lambs are again weighed, and the feed consumed calculated. The lambs are then necropsied. Ten animals per treatment are dressed, and the average cross-sectional area of the longissimus dorsi measured at the 12th rib and at the 7th lumbar vertebra measured. The data obtained are reported in Table IX.

TABLE IX

Evaluation of Test Compound for Increasing the Growth Rate of Ruminants, Improving Feed Efficiency and Enhancing the Deposition of Muscle Tissue

| Av/Animal | Compound 4-Amino- -[(tert-butylamino)methyl]-3,5-dichlorobenzyl alcohol (ppm) in Diet | | | |
|---|---|---|---|---|
| | 0 | 1 | 10 | 100 |
| Initial wt. (kg) | 33.0 | 32.9 | 32.4 | 32.5 |
| Final wt. (kg) | 43.9 | 43.1 | 43.4 | 44.2 |
| ADG (g) | 196 | 180 | 195 | 209 |
| % ± control | — | −8.2 | −0.5 | +6.6 |
| kg feed consumed/8-wk. | 87.75 | 79.50 | 82.00 | 77.50 |
| % ± control | — | −9.4 | −6.6 | −11.7 |
| FE | 8.13 | 7.91 | 7.51 | 6.73 |
| % ± control | — | +2.7 | +7.6 | +17.2 |

TABLE IX-continued

Evaluation of Test Compound for Increasing the Growth Rate of Ruminants, Improving Feed Efficiency and Enhancing the Deposition of Muscle Tissue

| Av/Animal | Compound 4-Amino- -[(tert-butylamino)methyl]-3,5-dichlorobenzyl alcohol (ppm) in Diet | | | |
|---|---|---|---|---|
| | 0 | 1 | 10 | 100 |
| Dressed carcass wt. (kg) | 22.79 | 24.24 | 24.39 | 23.49 |
| Muscle cross-sectional area* (am$^2$) | 14.57 | 19.35 | 20.80 | 18.98 |
| % + control | — | +32.9 | +42.8 | +30.3 |

*Average of cross-sectional area of the longissimus dorsi measured at 12th rib and at the 7th lumbar vertebra.

EXAMPLE 8

α-[(Tert-butylamino)methyl]-3,5-dichlorobenzyl Alcohol Hydrochloride

A solution containing 3.5 g of 3,5-dichlorostyrene oxide in 50 ml of absolute ethanol and 20 ml of t-butylamine is heated gently at reflux for 8 hours and the mixture is evaporated to dryness. The clear yellow syrup is dissolved in 75 ml of ethanol and 25 ml of H$_2$O, and the solution is cooled to 5° C. and acidified with 3N HCl. This solution is evaporated to dryness in vacuo and the residual white solid is recrystallized from acetone to afford 2.81 g, m.p. 218°–221° C.

Anal. Calc'd for C$_{12}$H$_{17}$NOCl$_2$HCl: C, 48.26; H, 6.08; H, 4.69. Found: C, 48.49; H, 6.17; N, 4.66.

The free base of the title compound is obtained by neutralization of the title compound with aqueous 10% NaOH. Other salts of the free base are then obtained by treatment of the free base in the above-mentioned procedure (aqueous ethanol) with addition of the appropriate acids, such as H$_2$SO$_4$, H$_3$PO$_4$, HNO$_3$, CH$_3$SO$_3$H, toluenesulfonic acid and pamoic acid.

The intermediate 3,5-dichlorostyrene oxide needed for preparing the title compound is made by reducing 28.4 g of 3,5-dichlorophenacyl bromide in 125 ml of absolute ethanol at 5° C. with 8 g of NaBH$_4$, added portionwise. After the addition is completed, the reaction mixture is stirred 16 hours at ambient temperature, which is obtained by gradual melting of the ice bath overnight. The mixture is quenched with 100 ml of H$_2$O, the aqueous mixture is cooled to 5° C., and carefully acidified to pH 3 with concentrated HCl. The mixture is extracted with 300 ml of $CH_2Cl_2$ and the extract is dried over $MgSO_4$, filtered, and evaporated to dryness in vacuo to afford the epoxide as a clear yellow oil.

The phenacyl bromide intermediate for the above-mentioned styrene oxide is prepared by brominating 10 g of 3,5-dichloroacetophenone in 50 ml of $CHCl_3$/50 ml of EtOAc with 23.6 g of $CuBr_2$. The mixture is heated at reflux for 2.5 hours and cooled to room temperature. After stirring for 16 hours at room temperature, the mixture is cooled in ice for 2 hours and filtered. The filter cake is washed with 50 ml of $CHCl_3$ and the combined filtrates are twice decolorized with activated carbon, filtered, and evaporated to dryness in vacuo to afford the orange oil of the 3,5-dichlorostyrene oxide.

EXAMPLE 9

The following 3,5-dichlorophenyl compounds (A) related to the title compound of Example 6 are prepared by the method described in Example 6 by substituting t-butyl amine with $R_2R_3NH$ amines.

| Compound | $R_2$ | $R_3$ | M.P. °C. |
| --- | --- | --- | --- |
| 1 | H | i-$C_3H_7$ | 97–103 |
| 2 | H | 2-$C_4H_9$ | |

EXAMPLE 10

α-[(Tert-butylamino)methyl]-3,5-dibromobenzyl Alcohol Hydrochloride

This title compound is prepared from 3,5-dibromostyrene oxide in the same manner as described in Example 6. The starting materials for this styrene oxide are similarly prepared starting with 3',5'-dibromoacetophenone.

The corresponding α-[(isopropylamino)methyl]-3,5-dibromobenzyl alcohol hydrochloride is prepared by substituting isopropyl amine for t-butyl amine.

EXAMPLE 11 m-Hydroxy-α-[(isopropylamino)methyl]benzyl Alcohol Hydrochloride

In 135 ml of 95% ethanol, 36.75 g of m-hydroxyacetophenone, 36.5 g of benzyl chloride, 1.75 g of KI, and 24.6 g of $K_2CO_3$ are stirred and heated at reflux for 5 hours. The mixture is cooled, evaporated in vacuo to remove ethanol and 100 ml of $H_2O$ is added. The mixture is then extracted with diethyl ether three times to afford 350 ml of extract, which is further washed with 50 ml of $H_2O$, saturated $NaHCO_3$ solution (2×50 ml), 50 ml of $H_2O$, and 50 ml of brine in succession. The filtrate is dried over $Na_2SO_4$ and evaporated to dryness. The residual oil is distilled to afford 49.13 g of m-benzyloxyacetophenone, b.p. 145°–147° C./0.2 mm. Bromination of 186 g of this acetophenone is accomplished with 349 g of $CuBr_2$ in 1 l of $CHCL_3$/1.5 l of ethanol heated at reflux. A $N_2$ sweep is used to remove HBr generated. After 4 hours, the mixture is filtered and the filter cake is washed with $CHCl_3$ (2×100 ml). The filtrate is evaporated in vacuo to afford an oil, which is dissolved in 200 ml of absolute ethanol (2×50 ml), and dried to afford 64.28 g m-benzyloxyphenacyl bromide, m.p. 57°–58° C. Further cooling of the filtrate affords 34 g. A 64 g-sample of the phenacyl bromide is added to a stirred mixture containing 212 ml of i-propylamine in 425 ml of ethanol under $N_2$ atmosphere at 5° C. The temperature rises to 12° C. and a clear solution is obtained. The solution is poured into ice (2 L) containing 500 ml of concentrated HCl and 1500 ml of $H_2O$. After stirring for 20 minutes, the mixture is filtered and the solid is washed with $H_2O$. On drying this gives 98.64 g, m.p. 200°–203° C. dec. This solid is dissolved in 400 ml of refluxing methanol, 400 ml of isopropyl alcohol is added, and the solution is concentrated to 400 ml. On cooling and collecting crystals, 54.36 of ketoamine melting at 213°–215° dec is obtained. This material (16 g) is added to 150 ml of methanol which contains 2 g of 5% Pd/carbon and hydrogenated in a Paar vessel at 42 p.s.i.g. of $H_2$. The mixture is filtered and the filtrate is evaporated. The residue is mixed with 50 ml of isopropyl alcohol and evaporated to dryness to afford a syrup, which is mixed with 100 ml of ethanol. The crystals are collected, washed with diethyl ether and dried to give 10.77 g, m.p. 129°–132° C., of the title compound.

By substituting tert-butylamine for isopropylamine, m-hydroxy-α-[(tert-butylamino)methyl]benzyl alcohol hydrochloride, m.p. 150°–154° C. dec. is obtained. Substitution of isopropylamine with diisopropylamine, benzylamine and allyamine affords m-hydroxy-α-[(diisopropylamino)methyl]benzyl alcohol, m-hydroxy-α-[(benzylamino)methyl]benzyl alcohol, and m-hydroxy-α-[(allylamino)methyl]benzyl alcohol hydrochlorides, respectively.

EXAMPLE 12

4-Amino-α-[(tert-butylamino)methyl]-3,5-diiodobenzyl Alcohol Hydrochloride

In 10 ml of acetic acid, 0.42 g of p-amino-α-[(tert-butylamino)methyl]benzyl alcohol is stirred under $N_2$ atmosphere and 0.48 g of N,N-dichlorobenzenesulfonamide and 0.6 g of NaI are stirred under $N_2$ atmosphere for 20 minutes. After 3 days, the mixture is poured into ice and the mixture is basified with 50% aq. NaOH. This mixture is extracted with $CH_2Cl_2$ (3×25 ml) and chromatographed on a $SiO_2$ plate using 1% $NH_4OH$/20% $CH_3OH$/$CH_2Cl_2$ to afford 0.22 g of the title compound. The reaction is repeated on a larger scale (8X) and the eluted crude product is dissolved in 100 ml of ethanol/10 ml of $H_2O$, stirred and 10% HCl is added to give pH 3. The mixture is evaporated to dryness in vacuo. Isopropyl alcohol is added and the mixture is evaporated to dryness. This process is repeated twice and the residue is crystallized from methanol/isopropyl alcohol by allowing methanol to evaporate until crystals form (methanol is used to dissolve the crude material before isopropyl alcohol is added). On cooling, 2 g of the title compound is obtained melting at 187° C. dec.

Anal. Calc'd for $C_{12}H_{19}ClI_2N_2O$: C, 29.02; H, 2.86; N, 5.64. Found: C, 29.11; H, 3.64; N, 5.64.

EXAMPLE 13

α-[(Tert-butylamino)methyl]-3,5-dichlorobenzyl Alcohol Hydrochloride

An alternate procedure for preparing the title compound and the compounds described in Example 7 is exemplified. Thus, 10 g of 4-amino-α-[(tert-butylamino)methyl]-3,5-dichlorobenzyl alcohol is added to 100 ml of 50–52% $H_3PO_2$ and the mixture is stirred and cooled to 8° C. in ice while 2.77 g of $NaNO_2$ in 15 ml of $H_2O$ is added over 65 minutes. Foaming occurs and is controlled with antifoaming silicone. After 20 minutes, the mixture is stirred 2 hours without cooling. The mixture is then poured into ice-$H_2O$ mixture and 50% aq. NaOH solution is added until the mixture is alkaline. The alkaline mixture is extracted with $CH_2Cl_2$ three times to give 200 ml of solution, which is washed with 25 ml of 2% NaOH and dried over $MgSO_4$ and evaporated to dryness in vacuo to give 9.13 g of brown oil. On standing, the oil solidifies, and it is dissolved in 100 ml of ethanol containing 10 ml of $H_2O$. The solution is acidified to pH 3 with 10% HCl and evaporated to dryness. The residue is treated with 50 ml of isopropyl alcohol and evaporated to dryness. This procedure is repeated to afford an off-white solid which is dissolved in methanol. The solution is evaporated in vacuo to afford a syrup, which is diluted with 50 ml of isopropyl alcohol and allowed to stand. The crystals which form are collected, washed with isopropyl alcohol and dried to yield 7.8 g, m.p. 217°–221° C. dec., of the title compound.

The compound described in Example 10 is similarly prepared. Deamination of 4-amino-3,5-dibromo-α-[(tert-butylamino)methyl]benzyl alcohol affords 3,5-dibromo-α-[(tert-butylamino)methyl]benzyl alcohol, m.p. 249°–251° C. dec.

EXAMPLE 14

4-Amino-3,5-dichloro-β-methoxyphenethylamine hydrochloride

Under $N_2$ atmosphere, 11 g of 4-amino-α-[(tert-butylamino)methyl]-3,5-dichlorobenzyl chloride is added to 75 ml of methanol at 0° C. After 20 minutes, the cooling bath is removed and the reaction mixture is stirred at ambient temperature. After the reaction is completed, the mixture is evaporated to dryness in vacuo. The residue is stirred in 75 ml of $H_2O$ and the mixture is made alkaline with 6N NaOH solution and extracted with $CH_2Cl_2$ (3×50 ml). The organic phases are dried over $MgSO_4$ and evaporated to dryness to afford an orange oil. This oil is dissolved in 150 ml of absolute EtOH and acidified with HCl/isopropyl alcohol solution to pH 2. The solution is evaporated to dryness and the residue is stirred in 75 ml of ethyl acetate. After cooling, this affords a pale yellow solid which is collected to give 6.97 g of the title compound, m.p. 195°–198° C. dec.

Similarly, substitution of ethyl alcohol, isopropyl alcohol, n-butyl alcohol and n-hexyl alcohol affords the corresponding β-ethoxy, β-isopropoxy, n-butoxy, and n-hexyloxy phenethylamine hydrochlorides.

EXAMPLE 15

4-Amino-α-[(tert-butylamino)methyl]-3,5-dichlorobenzyl chloride

Under $N_2$ atmosphere, 27.72 g of 4-amino-α-[(tert-butylamino)methyl]-3,5-dichlorobenzyl alcohol is added to 200 ml of thionyl chloride stirred at 0–5%C. After addition is completed, the reaction mixture is stirred at ambient temperature for 3 hours. Subsequently, the mixture is evaporated to dryness in vacuo to afford 37.34 g of yellow solid, which is used as is.

EXAMPLE 16

Alternate Procedure for 4-Amino-3,5-dichloro-β-methoxyphenethylamine hydrochloride In 100 ml of methanol, 10 g of 4-amino-α-[(tert-butylamino)methyl]-3,5-dichlorobenzyl alcohol is stirred in an ice bath and dry HCl gas is introduced into the solution. After saturation of the solution, the mixture is stirred at room temperature for an hour and evaporated to dryness. The solid is then stirred in ethyl acetate to afford the title product, which is collected by filtration.

EXAMPLE 17

N-tert-butyl-3,5-dichloro-β-methoxy-4-methylaminophenethylamine hydrochloride

A 7 g sample of α-[(tert-butylamino)methyl]-3,5-dichloro-4-methylaminobenzyl alcohol is added to 70 ml of thionyl chloride under $N_2$ atmosphere and the mixture is stirred for two hours. Excess thionyl chloride is removed in vacuo, and the glassy residue is dissolved in 50 ml of methanol. The solution is stirred for 1.5 hours and evaporated to dryness. The residue is dissolved in 100 ml of $H_2O$ and extracted with 2×50 ml of $CH_2Cl_2$. The aqueous layer is neutralized with solid $NaHCO_3$ and extracted with $CH_2CL_2$. The extract is dried ($MgSO_4$) and evaporated to dryness in vacuo to give 4.1 g of semi-solid, which after trituration with ethyl ether affords 1.07 g of the title compound, mp 220°–221° C. Similarly, the following ethers are prepared:

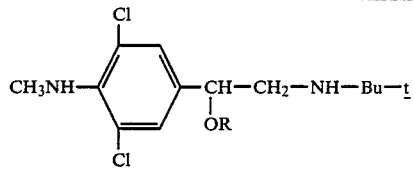

| Alcohol | |
| --- | --- |
| ethanol | $C_2H_5$ |
| 1-propanol | 1-$C_3H_7$ |
| 2-propanol | 2-$C_3H_7$ |
| 1-butanol | 1-$C_4H_9$ |
| 2-butanol | 2-$C_4H_9$ |
| 1-hexanol | n-$C_6H_{13}$ |
| benzyl alcohol | benzyl |
| allyl alcohol | allyl |
| 4-methoxybenzyl alcohol | 4-methoxybenzyl |
| 4-chlorobenzyl alcohol | 4-chlorobenzyl |
| 4-nitrobenzyl alcohol | 4-nitrobenzyl |
| 4-methylbenzyl alcohol | 4-methylbenzyl |
| 3,4-dimethylbenzyl alcohol | 4-methylbenzyl |
| 3,4-dimethoxybenzyl alcohol | 3,4-dimethoxybenzyl |
| 3,4-dichlorobenzyl alcohol | 3,4-dichlorobenzyl |
| 2-chlorobenzyl alcohol | 2-chlorobenzyl |
| 2-methylbenzyl alcohol | 2-methylbenzyl |

EXAMPLE 18

N-tert-Butyl-3,5-dichloro-β-methoxyphenethylamine hydrochloride

A mixture containing 6.55 g of 4-amino-N-tert-butyl-3,5-dichloro-β-methoxyphenethylamine hydrochloride in 66 ml of 50% hypophosphorous acid is cooled to 5° C. and 1.52 g of $NaNO_2$ in 15 ml of $H_2O$ is added dropwise. Rapid foaming occurs from gas evolution and after 0.5 hours at 5° C., the mixture is stirred further at room temperature for two hours. It is then made alkaline with 50% aqueous NaOH solution, and the mixture is kept at below 25° C. with addition of ice. The mixture is extracted with 3×100 ml of $CH_2Cl_2$ and the combined organic phases are washed with 200 ml of brine, dried ($MgSO_4$), and evaporated to dryness in vacuo to give 5.1 g of the title compound in the form of the free base. This product is dissolved in 50 ml of EtOH and acidified at 5° with 4N HCl to afford a light orange precipitate, which is collected. This gives 3.36 g, mp 278°–280° dec, of the title compound which is recrystalized from isopropanol to give 2.35 g, mp 280° C. dec.

Similarly, N-isopropyl-3,5-dichloro-β-methoxyphenethylamine hydrochloride is prepared from 4-amino-N-isopropyl-3,5-dichloro-β-chlorophenethylamine hydrochloride.

EXAMPLE 19

In the manner described in Example 17, the following ethers are prepared by substituting the corresponding alcohols for methanol.

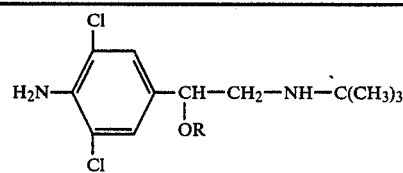

| R | mp °C. |
|---|---|
| Ethyl (.HCl) | 180–182 |
| 2-Propyl | 117–121 |
| benzyl | 190–193 |
| allyl | 57–59 |
| 1-hexyl | |
| 4-methoxybenzyl | |
| 4-chlorobenzyl | |
| 4-nitrobenzyl | |
| 4-methylbenzyl | |
| 3,4-dimethylbenzyl | |
| 3,4-dimethoxybenzyl | |
| 3,4-dichlorobenzyl | |
| phenyl | oil |
| 4-chlorophenyl | |
| 4-methoxyphenyl | |
| 4-methylphenyl | |
| 2-chlorophenyl | |
| 4-nitrophenyl | |

EXAMPLE 20

N-tert-Butyl-3-chloro-5-cyano-B-methoxy-4-aminophenethylamine hydrochloride

In the manner described in Example 17, α-[(tert-butylamino)methyl]-4-amino-3-chloro-5-cyanobenzyl alcohol is converted into the title compound; and, similarly, the following are also prepared:

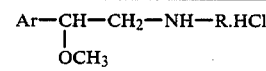

| Ar | R |
|---|---|
| 4-amino-3,5-dicyanophenyl | t-butyl |
| 4-amino-3-chloro-5-trifluoro-methylphenyl | t-butyl |
| 4-amino-3-chloro-5-trifluoro-methylphenyl | i-propyl |
| 4-acetamido-3,5-dichlorophenyl | t-butyl |
| 4-acetamidophenyl | t-butyl |
| 4-amino-3-chloro-5-$H_2N$—CO—phenyl | t-butyl |
| 4-amino-3-chloro-5-HO—CO—phenyl | t-butyl |
| 4-amino-3-chloro-5-methylphenyl | t-butyl |
| 4-amino-3-chloro-5-methoxyphenyl | t-butyl |
| 4-amino-3-chloro-5-nitrophenyl | t-butyl |
| 4-amino-3-chloro-5-$CH_3O$—CO—phenyl | t-butyl |
| 4-amino-3-chloro-5-dimethyl-aminomethylphenyl | t-butyl |
| 4-amino-3-cyano-phenyl | t-butyl |

EXAMPLE 21

5-(4-amino-3,5-dichlorophenyl)-3-tert-butyl-2-oxazolidinone

In 10 ml of $CH_2CL_2$, 0.5 g of 4-amino-α-[(tert-butylamino)methyl]-3,5-dichlorobenzyl alcohol is stirred with 1 ml of $Et_3N$ at −5° C. and 2 ml of 12.5% $COCl_2$ in benzene/5 ml of $CH_2CL_2$ is added over 15 minutes. The resulting suspension is stirred 20 minutes at 1° C. and allowed to warm to room temperature with stirring for 1.5 hours. The mixture is evaporated to dryness, and the residue is chromatographed on silica gel with 1:1 hexane/$CH_2CL_2$ to afford 0.1 g of oil which crystallizes to give the title compound, mp 97°–103° C.

In the same manner, α-[(allylamino)methyl]-4-amino-3,5-dichlorobenzyl alcohol is allowed to react with phosgene to afford 5-(4-amino-3,5-dichlorophenyl)-3-allyl-Z-oxazolidinone.

Likewise, the following compounds are prepared by this manner:

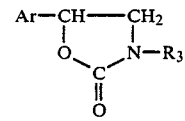

| Ar | $R_3$ |
|---|---|
| 3,5-dichlorophenyl | t-butyl |
| 3,5-dichlorophenyl | i-propyl |
| 4-acetamidophenyl | i-propyl |
| 4-amino-3-chloro-5-cyanophenyl | t-butyl |
| 4-amino-3-chloro-5-trifluoromethylphenyl | t-butyl |
| 3-chloro-4-acetamidophenyl | t-butyl |
| 3,5-dichloro-4-methylaminophenyl | t-butyl |
| 3,5-dichloro-4-ethylaminophenyl | t-butyl |
| 3,5-dichloro-4-i-propylaminophenyl | t-butyl |
| 3,5-dichloro-4-acetamidophenyl | t-butyl |
| 3,5-dichloro-4-methoxycarbonylaminophenyl | t-butyl |
| 3,5-dichloro-4-benzyloxycarbonylaminophenyl | t-butyl |
| 3,5-dichloro-4-methylcarbamoylaminophenyl | t-butyl |
| 4-amino-3-chloro-5-methylphenyl | t-butyl |

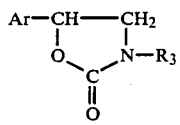

| Ar | R₃ |
| --- | --- |
| 4-amino-3-cyanophenyl | t-butyl |
| 4-amino-3-trifluoromethylphenyl | t-butyl |
| 4-amino-3-chloro-5-NH₂CO—phenyl | t-butyl |
| 4-amino-3-chloro-5-HOOC—phenyl | t-butyl |
| 4-amino-3-chloro-5-CH₃OOC—phenyl | t-butyl |
| 4-amino-3-chloro-5-(CH₃)₂NCH₂—phenyl | t-butyl |
| 4-amino-3,5-dicyanophenyl | t-butyl |

EXAMPLE 22

4-Amino-α-[(tert-butylamino)methyl]-3,5-dichlorobenzyl alcohol acetate

A mixture containing 1 g of 4-amino-α-[(tert-butylamino)methyl]-3,5-dichlorobenzyl alcohol in 35 ml of CH₂Cl₂ at 10°–15° C. is stirred, and 0.37 g of Ac₂O and 0.5 ml of Et₃N are added dropwise. The reaction mixture is then allowed to warm to room temperature, and the reaction is followed by thin-layer chromatography to completion. The mixture is evaporated to dryness in vacuo, and the yellow viscous liquid (1.5 g) is stirred with 50 ml of ethyl ether to afford a yellow solid (0.84 g), mp 128°–131° C. This material is shown by nuclear magnetic resonance spectroscopy and by neutralization with alkali to be the acetic acid salt. On treating 100 mg of this salt in 30 ml of CH₂Cl₂ with 30 ml of 10% aqueous NaOH, the salt is neutralized. The CH₂Cl₂ solution is dried (MgSO₄) and evaporated to dryness in vacuo to afford the viscous title compound. Analysis: Calc'd for C₁₄H₂₀O₂N₂Cl₂: C, 52.67; H, 6.32; N, 8.78; Found: C, 52.38; H, 6.51; N, 8.88.

In the same manner, propionic anhydride, butyric anhydride, pivalic anhydride, and benzoic anhydride are allowed to react with 4-amino-α-[(tert-butylamino)methyl]-3,5-dichlorobenzyl alcohol (A) and α-[(tert-butylamino)methyl]-3,5-dichloro-4-methylaminobenzyl alcohol (B) respectively, to afford the propionate, butyrate, pivalate and benzoates of A and B.

EXAMPLE 23

The following esters are prepared by the method of Example 22 by using the appropriate acid anhydride.

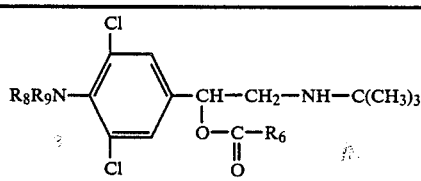

| R₈ | R₉ | R₆ |
| --- | --- | --- |
| H | CH₃ | CH₃ |
| H | C₂H₅ | CH₃ |
| H | n-C₃H₇ | CH₃ |
| H | 2-C₃H₇ | CH₃ |
| H | benzyl | CH₃ |
| H | allyl | CH₃ |
| CH₃ | CH₃ | CH₃ |
| H | CH₃ | C₂H₅ |
| H | CH₃O—CO— | CH₃ |
| H | CH₃NH—CO | CH₃ |
| H | CH₃ | n-C₄H₉ |
| C₂H₅ | C₂H₅ | CH₃ |
| n-C₄H₉ | n-C₄H₉ | CH₃ |

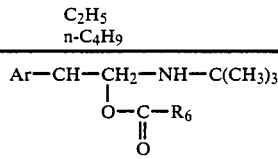

| Ar | R₆ |
| --- | --- |
| 3,5-dichlorophenyl | 2-C₃H₇ |
| 4-amino-3-chloro-5-cyanophenyl | CH₃ |
| 4-amino-3-chloro-5-trifluoromethylphenyl | CH₃ |
| 4-amino-3-chloro-5-H₂NCO—phenyl | CH₃ |
| 4-amino-3-chloro-5-HOOC—phenyl | CH₃ |
| 4-amino-3-chloro-5-methylphenyl | CH₃ |
| 4-amino-3-bromo-5-cyanophenyl | CH₃ |
| 4-amino-3-chloro-5-CH₃OCO—phenyl | CH₃ |
| 4-amino-3-chloro-5-(CH₃)₂NCH₂—phenyl | CH₃ |
| 4-amino-3,5-dicyanophenyl | CH₃ |
| 4-amino-3-cyanophenyl | t-C₄H₉ |

EXAMPLE 24

N-(4-amino-3,5-dichloro-β-hydroxyphenethyl)-N-tert-butylacetamide acetate

A mixture containing 2.5 g of 4-amino-α-[(tert-butylamino)methyl]-3,5-dichlorobenzyl alcohol, 25 ml of pyridine and 10 ml of acetic anhydride is stirred for three hours and evaporated to dryness in vacuo with heating up to 70° C. The residue is treated with ice, 100 ml of CH₂Cl₂ and 50 ml of 10% NaOH solution. The CH₂Cl₂ phase is separated, and the aqueous portion is further extracted with CH₂CL₂ (2×50 ml). The combined CH₂CL₂ solutions are dried (Na₂SO₄) and evaporated to dryness to afford a solid after scratching. The solid is washed with hexane and collected to afford 2.61 g of the title compound, mp 126°–136° C.

Similarly, by substituting the appropriate acid anhydrides, the following compounds are prepared.

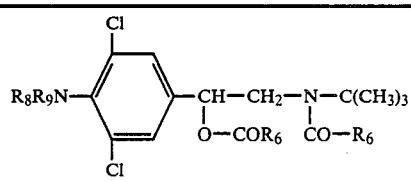

| R₈ | R₉ | R₆ |
| --- | --- | --- |
| H | CH₃ | CH₃ |
| H | C₂H₅ | CH₃ |
| H | 2-C₃H₇ | CH₃ |
| H | n-C₄H₉ | CH₃ |
| CH₃ | CH₃ | CH₃ |
| H | CH₃O—O | CH₃ |
| H | CH₃NH—CO | CH₃ |
| H | CH₃CO | CH₃ |
| H | CH₃ | C₂H₅ |
| C₂H₅ | C₂H₅ | n-C₄H₉ |

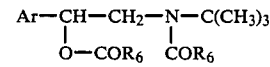

| Ar | R₆ |
| --- | --- |
| 4-amino-3,5-dicyanophenyl | C₂H₅ |
| 4-amino-3-chloro-t-dimethylamino methylphenyl | CH₃ |
| 4-amino-3-chloro-5-CH₃OOC—phenyl | C₂H₅ |
| 4-amino-3-chloro-5-methylphenyl | CH₃ |
| 3,5-dichlorophenyl | CH₃ |
| 4-amino-3-chloro-5-cyanophenyl | CH₃ |
| 4-amino-3-chloro-5-trifluoromethylphenyl | CH₃ |

-continued

| | |
|---|---|
| 4-amino-3-chloro-5-H$_2$NCO—phenyl | CH$_3$ |

EXAMPLE 25

4-Acetamido-α-[(tert-butylamino)methyl]-3,5-dichlorobenzyl alcohol acetate

In 15 ml of CH$_2$CL$_2$, 1.57 g. of 4-acetamido-β-[(tert-butylamino)methyl]-3,5-dichlorobenzyl alcohol is suspended and stirred while 1.2 g of triethylamine in 30 ml of 30 ml of CH$_2$Cl$_2$ is added, followed by 0.7 g of acetic anhydride in 15 ml of CH$_2$CL$_2$. The mixture is stirred for 20 hours and then is washed with 100 ml of 10% NaOH solution. The organic phase is separated, dried (Na$_2$SO$_4$) and evaporated to dryness in vacuo. The residue is dissolved in 30 ml of ethanol and a trace of H$_2$O is added, followed by 10% HCl to acidify. The mixture is evaporated to dryness in vacuo and the residue is crystallized from acetone/hexane (30 ml/5 ml). This affords 1.35 g, mp. 254°–257° C. dec., of the title compound.

Similarly, by replacing acetic anhydride with propionic anhydride, butyric anhydride, pivalic anhydride, and benzoic anhydride, the corresponding propionate, butyrate, pivalate, and benzoate esters are prepared.

EXAMPLE 26

N-Isopropyl-n-hydroxy-β-methoxyphenethylamine hydrochloride

In 425 ml of ethanol, 64 g of 3-benzyloxyphenacyl bromide and 212 ml of iso-propylamine are stirred at 5° C. under N$_2$ atmosphere, and the temperature is allowed to rise to 12° C. After 0.75 minutes, the clear solution is poured into 2 liters of crushed ice containing 500 ml of concentrated HCl and 1.5 liters of H$_2$O. The mixture is stirred for 20 minutes, filtered and the solid is washed with water to afford 3'-(benzyloxy)-2-isopropylamino-acetophenone hydrochloride, mp 213°–215° C. dec. A 5 g.-sample of this material is stirred in 50 ml of methanol, and the mixture is cooled in ice and neutralized with 10% NaOH until a clear solution is obtained. To this solution, 2 g of NaBH$_4$ is added and after 0.75 hours of stirring, the mixture is evaporated in vacuo, and the resulting solid is collected and washed with H$_2$O. This gives, after drying, 4.4 g of m-(benzyloxy)-α-[(isopropylamino)methyl]benzyl alcohol, mp 83°–85° C.

This alcohol is then treated in the manner described in Example 17 to afford N-isopropyl-m-benzyloxy-β-methoxyphenethylamine hydrochloride, which is then debenzylated with H$_2$/5% palladium-carbon at 50 p.s.i.g. in 2-propanol. After filtering and evaporating to dryness, this procedure affords N-isopropyl-m-hydroxy-β-methoxyphenethylamine hydrochloride.

In the same manner, N-tert-butyl-m-hydroxy-β-methoxyphenethylamino hydrochloride is prepared starting with 3'-(benzyloxy)-2-tert-butylaminoacetophenone.

EXAMPLE 27

α-[(tert-Butylamino)methyl]-m-hydroxybenzyl alcohol acetate

In the manner described in Example 25, m-(benzyloxy)-α-[(tert-butylamino)methyl]benzyl alcohol is converted to m-(benzyloxy)-α-[(tert-butylamino)methyl]-benzyl alcohol acetate. This material is then debenzylated by the procedure of Example 26 to give α-[(tert-butylamino)methyl]-m-hydroxybenzyl alcohol acetate.

EXAMPLE 28

5-(p-Aminophenyl)-3-tert-butyl-2-oxazolidinone

In 270 ml of CH$_2$Cl$_2$, 12.97 g of α-[(tert-butylamino)-methyl]-p-nitrobenzyl alcohol is dissolved. The solution is cooled to −5° C. and 54 ml of 12.5% phosgene in benzene is added slowly. After the addition is completed, the mixture is stirred for 3.5 hours and poured on ice. The organic phase is separated, and the aqueous layer is extracted with CH$_2$Cl$_2$ (2×100 ml). The combined organic layers are washed with saturated NaHCO$_3$ solution (2×250 ml), 100 ml of H$_2$O and dried over MgSO$_4$. The solution is evaporated to dryness to give 16.3 g, which is recrystallized from MeOH twice to afford 12.58 g of 3-tert-butyl-5-(p-nitrophenyl)-2-oxazolidinone, mp 123°–125° C. This product (10 g) is dissolved in 200 ml of MeOH and hydrogenated over 6 g of Raney nicke at 51 p.s.i.g at 40° C. to give, after filtration and evaporation, 8.21 g of 5-(p-aminophenyl)-3-tert-butyl-2-oxazolidinone, mp 125°–129° C.

EXAMPLE 29

α-[(tert-butylamino)-methyl]3,5-dichloro-4-dimethylaminobenzyl alcohol

A mixture containing 50 g of p-fluoroacetophenone and 150 ml of 40% aqueous dimethylamine is warmed in a pressure bottle at 90°–100° C. After two hours, a pale yellow oil is formed. The mixture is cooled, and the oil solidifies. The solid is collected and washed well with H$_2$O to give 54.93 of p-dimethylaminoacetophenone, mp 101°–103° C., after heptane recrystallization. A 72 g sample of this acetophenone is heated with 129 g of N-chlorosuccinimide in 700 ml of toluene to reflux temperature and maintained at this temperature for 35 minutes. The mixture is cooled and filtered. The filter cake is washed with 200 ml of toluene, and the filtrate and wash solution are evaporated to dryness in vacuo to afford 66 g of oil. This oil is chromatographed on SiO$_2$ with 40% hexane/CH$_2$Cl$_2$ to give 38.9 g of 3.5-dichloro-4-dimethylaminoacetophenone as a yellow oil. A 5.22 g sample of this oil is added portionwise to 2.75 g of SeO$_2$ in 20 ml of dioxane and 0.7 ml of H$_2$O at 55°–60° C. This mixture is heated at reflux temperature for 4.5 hours, cooled and filtered through siliceous earth. The filter cake is washed with 20 ml of dioxane. The dioxane solutions are cooled to 15° C. and 2.77 g of t-butylamine is added dropwise to afford a tan precipitate. After stirring 15 minutes at room temperature, the mixture is diluted with 200 ml of ethanol, cooled to 5° C. and 7 g of NaBH$_4$ is added portionwise. After 15 hours, the mixture is treated with 300–400 g of ice and 200 ml of H$_2$O at below 10° C. The mixture is stirred to dissolve all solids and extracted with 300 ml of CH$_2$Cl$_2$. The CH$_2$Cl$_2$ layer is washed with 100 ml of H$_2$O, dried (MgSO$_4$) and evaporated to dryness in vacuo to give 5.6 g of orange oil. This oil is dissolved in ethyl ether, decolorized with activated carbon and concentrated to 15 ml. On cooling, crystals are obtained. The title product is collected as white crystals, mp 96°–99° C.

EXAMPLE 30

5-(4-amino-3,5-dibromophenyl)-3-tert-butyloxazolidine

A mixture containing 2 g of 4-amino-3,5-dibromo-α-[(tert-butylamino)methyl]benzyl alcohol and 5 ml of 37% formalin solution in 20 ml of toluene containing a few crystals of p-toluene sulfonic acid is heated at reflux to azeotrope water. After three hours, the mixture is cooled, diluted to 75 ml with $CH_2Cl_2$ and washed with 10% aqueous NaOH solution (2×20 ml). The aqueous portion is further extracted with 10 ml of $CH_2Cl_2$ and the combined organic extracts are dried ($MgSO_4$) and evaporated to dryness in vacuo to afford 1.6 g of clear brown oil. A chemical ionization mass spectrographic analysis gives a Mass+$H^+$ of 377, which is correct for the title compound. The nuclear magnetic resonance proton spectrum reveals a singlet at $\delta 4.53$ in $CDCl_3$ indicative of the O—$\overline{CH_2}$—N group in the title compound.

In the same manner, the following oxazolidines are prepared by substituting the corresponding arylethanolamines for 4-amino-3,5-dibromo-α-[tert-butylamino)methyl]benzyl alcohol.

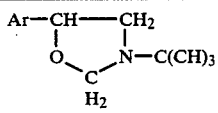

Ar 4-amino-3,5-dichlorophenyl
4-methylamino-3,5-dichlorophenyl
4-amino-3-chloro-5-cyanophenyl
4-amino-3-chloro-5-trifluromethylphenyl
4-amino-3-chloro-5-methylphenyl
4-amino-3-bromo-5-$NH_2$—CO—phenyl
4-amino-3-bromo-5-HOOC—phenyl
4-acetamido-3,5-dichlorophenyl
3,5-dichloro-4-methoxycarbonylaminophenyl
3,5-dichloro-4-methylcarbamoylaminophenyl
4-amino-3-cyanophenyl
4-amino-3-trifluoromethylphenyl
4-amino-3,5-dicyanophenyl

EXAMPLE 31

4-Benzylamino-α-[tert-butylamino)methyl]-3,5-dichlorobenzyl alcohol

In the manner described in Example 29, the title compound is prepared to give mp 86°–89° C.

EXAMPLE 32

4'-[2-(tert-butylamino)-1-hydroxyethyl]-2',6'-dichlorobenzanilide

A mixture containing 2.04 g of 4-amino-3,5-dichloroacetophenone and 0.25 ml of triethylamine in 10 ml of benzoyl chloride is stirred and heated at 130°–135° C. for two hours. The mixture is cooled, filtered and the product is washed with ether. This amide is further oxidized with $SeO_2$ in the manner described in Example 29 to eventually afford the title compound, mp 177°–182° C.

EXAMPLE 33

α-[tert-butylamino)methyl]-3,5-dichloro-4-methylaminobenzyl alcohol p-Methylaminoacetophenone is prepared and chlorinated by method described in Example 29 to give 3,5-dichloro-4-methylaminoacetophenone. This ketone (18 g) in 200 ml of $CHCl_3$ is stirred and 4.65 ml of $Br_2$ in 50 ml of $CHCl_3$ is added dropwise. After the addition is completed, the mixture is stirred an additional 20 minutes and warmed to reflux temperature for 25 minutes. The mixture is cooled, 100 ml of $H_2O$ is added and saturated $Na_2CO_3$ solution is added carefully until the mixture is neutral. The $CHCl_3$ layer is separated and the aqueous layer is further extracted with 100 ml of $CH_2Cl_2$. The combined extracts are dried ($MgSO_4$) and evaporated to dryness to afford 16.3 g of the phenacyl bromide. This material (16 g) in 80 ml of EtOH is stirred at 12°–15° C. and 40 ml of t-butylamine is added dropwise. After the addition is completed the mixture is stirred for 10 minutes at 12°–15° C. and then cooled to 5° C. and 4 g of $NaBH_4$ is carefully added. After stirring for 0.5 hours, the mixture is allowed to warm to room temperature and stirring is continued for 0.75 hours. The mixture is poured on 300 ml of ice with stirring and the resulting mixture is extracted with 300 ml of $CH_2Cl_2$. The $CH_2Cl_2$ extract is dried ($MgSO_4$) and evaporated to dryness in vacuo to give a yellow oil. Trituration of this residue with ethyl ether affords 7.45 g of the title compound, which melts at 98°–101° C. after recrystallization from ethyl ether.

EXAMPLE 34

5-[2-(tert-butylamino)-1-hydroxyethyl]anthranilontrile

A mixture containing 48.86 g of p-aminoacetophenone in 490 ml of toluene is stirred while 64.5 g of N-bromosuccinimide is added in portions over 0.5 hours at below 40° C. After 15 minutes, the mixture is washed with $H_2O$ (4×100 ml). The solution is dried ($MgSO_4$) and evaporated to dryness to afford 70.53 g of 4-amino-3-bromoacetophenone, mp 59°–62° C. A 35 g sample of this material in 180 ml of dry dimethylformamide is stirred and heated at reflux with 17.57 g of $Cu_2(CN)_2$ for 6 hours under $N_2$ atmosphere. Subsequently, 180 ml of $FeCl_3$/HCl solution (40 g $FeCl_3.6H_2O$/10 ml concentrated HCl/60 ml $H_2$) is added and the mixture is heated for 20 minutes at 60°–70° C. and poured into 350 ml of $H_2O$. The aqueous mixture is extracted with $CH_2Cl_2$ and the extracts are washed with $H_2O$, saturated $NaHCO_3$ solution and $H_2O$, respectively. The $CH_2Cl_2$ solution is evaporated to dryness in vacuo and the residue is recrystallized from 95% EtOH to afford 14.25 g, mp 155°–159° C., of 4-amino-3-cyanoacetophenone. A 4.8 g sample of this product in 100 ml of EtOAc and 100 ml of $CHCl_3$ containing 13.32 g of $CuBr_2$ is heated at reflux temperature for 20 minutes. The mixture is further heated after 20 ml of EtOH is added and then filtered while still hot. The filter cake is washed with 50 ml of hot 20% MeOH/$CH_2Cl_2$ and the combined organic solutions are evaporated to dryness in vacuo. The residue is stirred in 25 ml of $CH_2Cl_2$ and the solid is collected and washed with $CH_2Cl_2$ to give 8.08 g of the phenacyl bromide. This materials is added to 50 ml of t-$BuNH_2$ in 100 ml of EtOH at 5° under $N_2$ atmosphere. After 10 minutes of stirring, the mixture is allowed to warm to 30° C. to give a solution. This solution is cooled to 10° and 4 g of $NaBH_4$ is added in portions. After 45 minutes, the mixture is allowed to warm (42° C.) and kept at 20° C. until the exotherm subsides. The mixture is then evaporated to dryness and the residue is washed with $H_2O$. The residue is dried and treated with 200 ml of boiling MeOH and the hot MeOH solution is filtered. The filter cake is further washed with hot MeOH and the combined filtrate are concentrated to afford crystals. This solid is recrystallized from MeOH/2-PrOH to afford 2.08 g, mp 184°–186° C., of the title compound.

In a similar manner, the following related compounds are prepared starting with the appropriate acetophenone:

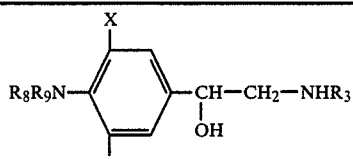

| R$_8$ | R$_9$ | R$_3$ | X |
|---|---|---|---|
| H | H | 2-C$_3$H$_7$ | H |
| H | CH$_3$ | t-butyl | H |
| CH$_3$ | CH$_3$ | t-butyl | H |
| H | CH$_2$H$_5$ | t-butyl | H |
| H | n-C$_3$H$_7$ | t-butyl | H |
| H | 2-C$_3$H$_7$ | t-butyl | H |
| H | n-C$_4$H$_9$ | t-butyl | H |
| H | CH$_3$ | 2-C$_3$H$_7$ | H |
| H | benzyl | t-butyl | H |
| C$_2$H$_5$ | C$_2$H$_5$ | t-butyl | Cl |
| n-C$_3$H$_7$ | n-C$_3$H$_7$ | t-butyl | Cl |
| n-C$_4$H$_9$ | n-C$_4$H$_9$ | t-butyl | Cl |

EXAMPLE 35

3-chloro-5-[2-(tert-butylamino)-1-hydroxyethyl]anthranilonitrile

In 100 ml of toluene, 5 g of 4-amino-3-cyanoacetophenone is heated at reflux temperature for 20 minutes with 4.2 g of N-chlorosuccinimide. The mixture is cooled and filtered. The filtrate is further heated at reflux temperature for 2 hours. The precipitate is collected and washed with H$_2$O. The remaining solid is treated with 0.75 ml of Br$_2$/14 ml of CHCl$_3$ added to 75 ml of CHCl$_3$ and 4.9 ml of EtOH. The mixture is evaporated to dryness and the residue is slurried with CH$_2$Cl$_2$, collected and washed with CH$_2$Cl$_2$ to afford 2.84 g of the phenacyl bromide. This material is allowed to react with t-BuNH$_2$ and reduced with NaBH$_4$ by the procedure of Example 34 to afford the title compound, mp 128°–138° C.

In a similar manner, the following compounds are prepared:

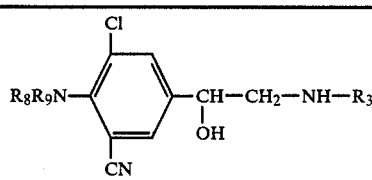

| R$_8$ | R$_9$ | R$_3$ |
|---|---|---|
| H | H | 2-propyl |
| H | CH$_3$ | t-butyl |
| CH$_3$ | CH$_3$ | t-butyl |
| H | C$_2$H$_5$ | t-butyl |
| H | 2-propyl | t-butyl |
| H | n-butyl | t-butyl |
| H | benzyl | t-butyl |

EXAMPLE 36

5-[2-(tert-butylamino)-1-hydroxyethyl]-3-chloroanthranilic acid, methyl ester, hydrochloride A mixture containing 1.36 g of 5-[2-(tert-butylamino)-1-hydroxyethyl]-3-chloroanthranilonitrile in 21 ml of 50% aqueous NaOH and 21 ml of EtOH is stirred under N$_2$ for 0.5 hours. The mixture is evaporated to remove EtOH and acidified to pH 3 and further evaporated to dryness in vacuo. The residue treated several times with MeOH and evaporated to dryness. The solid is then treated with a solution which is prepared from 40 ml of MeOH and 2 ml of acetyl chloride. After allowing to stand overnight, the mixture is filtered and the filtrate is evaporated to dryness. The filter cake is also washed with MeOH and added to preceding filtrate. The residue is dissolved in acetone, filtered, and evaporated to dryness. The solid is triturated with Et$_2$O and filtered to give 1.49 g, mp 95°–115° C., of the title compound.

In a similar manner, the following related esters are prepared:

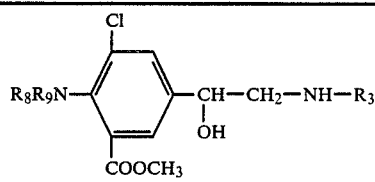

| R$_8$ | R$_9$ | R$_3$ |
|---|---|---|
| H | H | 2-propyl |
| H | CH$_3$ | t-butyl |
| CH$_3$ | CH$_3$ | t-butyl |
| H | C$_2$H$_5$ | t-butyl |
| H | n-propyl | t-butyl |
| H | n-butyl | t-butyl |
| H | benzyl | t-butyl |
| H | allyl | t-butyl |
| C$_2$H$_5$ | C$_2$H$_5$ | t-butyl |
| n-C$_4$H$_9$ | n-C$_4$H$_9$ | t-butyl |
| n-C$_3$H$_7$ | n-C$_3$H$_7$ | t-butyl |

EXAMPLE 37

2-Amino-3-bromo-5-[2-(tert-butylamino)-1-hydroxyethyl]benzamide

A mixture containing 1.02 g of 3-bromo-5-[2-(tert-butylamino)-1-hydroxyethyl]anthranilonitrile in 25 ml of H$_2$O, 5 ml of 50% NaOH and 30 ml of EtOH is stirred and heated at 55°–65° C. under N$_2$ atmosphere for 1.25 hours. The mixture is evaporated to remove EtOH and extracted with CHCl$_3$. The CHCl$_3$ extract is washed with 25 ml of 2% NaOH, dried (MgSO$_4$) and evaporated to dryness to afford 0.74 g. This solid is stirred with pentane and filtered to afford 0.6 g, mp 135°–145° C., of the title compound.

Similarly, the following compounds are prepared:

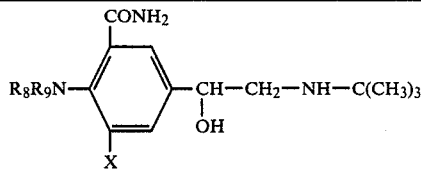

| R$_8$ | R$_9$ | X |
|---|---|---|
| H | CH$_3$ | Cl |
| H | H | Cl |
| H | C$_2$H$_5$ | Cl |
| CH$_3$ | CH$_3$ | Cl |
| H | 2-C$_3$H$_7$ | Cl |
| H | n-C$_4$H$_9$ | Cl |
| H | CH$_3$ | Br |
| H | benzyl | Cl |

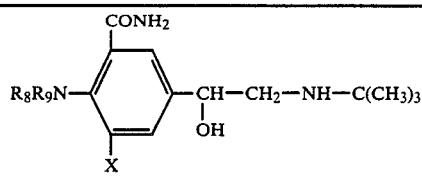

| R$_8$ | R$_9$ | X |
|---|---|---|
| C$_2$H$_5$ | C$_2$H$_5$ | Cl |
| n-C$_3$H$_7$ | n-C$_3$H$_7$ | Cl |
| n-C$_4$H$_9$ | n-C$_4$H$_9$ | Cl |

EXAMPLE 39

3-bromo-5-[2-(tert-butylamino)-1-hydroxyethyl]anthranilic acid

A mixture containing 2 g of 3-bromo-5-[2-(tert-butylamino)-1-hydroxyethyl]anthranilonitrile in 10 ml of 50% NaOH, 50 ml of H$_2$O and 60 ml of EtOH is stirred and heated to reflux temperature under N$_2$ for an hour. The EtOH is evaporated and the aqueous mixture mixed with 50 ml of H$_2$O and 50 ml of CHCl$_3$. The CHCl$_3$ layer is removed and the interfacial brown oil is collected, added to 10 ml of MeOH, 5 ml of H$_2$O and this mixture is acidified to pH 5. After stirring for an hour, the off-white solid is collected, washed with H$_2$O and dried to give 0.8 g, mp 221.5° C. dec., of the title compound.

Similarly, the following compounds are prepared:

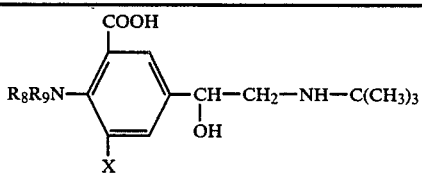

| R$_8$ | R$_9$ | X |
|---|---|---|
| H | H | Cl |
| H | CH$_3$ | Cl |
| CH$_3$ | CH$_3$ | Cl |
| H | CH$_3$ | Br |
| H | 2-C$_3$H$_7$ | Cl |
| H | n-C$_4$H$_9$ | Cl |
| H | benzyl | Cl |
| C$_2$H$_5$ | C$_2$H$_7$ | Cl |
| n-C$_3$H$_7$ | n-C$_3$H$_7$ | Cl |
| n-C$_4$H$_9$ | n-C$_4$H$_9$ | Cl |

EXAMPLE 40

5-(3-hydroxyphenyl)-3-tert-butyl-2-oxazolidinone

In the manner described in Example 21, m-benzyloxy)-α-[tert-butylamino)methyl]benzyl alcohol is coverted to the oxazolidinone compound by treatment with phosgene. Subsequently debenzylation is completed by the method of Example 26 to give the title compound.

EXAMPLE 41

5-(3-hydroxyphenyl)-3-tert-butyloxazolidine

In the manner described in Example 28, m-(benzyloxy)-α-[(tert-butylamino)methyl]benzyl alcohol is reacted with formaldehyde to afford the oxazolidine derivative, which is debenzylated by the procedure of Example 26 to give the title compound.

EXAMPLE 42

4-amino-N-tert-butyl-3,5-dichloro-β-(methylthio)-phenethylamine hydrochloride

In the manner described in Example 17, N-tert-butyl-3,5-dichloro-β-chloro-4-aminophenethylamine hydrochloride is prepared. An 11 g sample of this product is portionwise added to 5 ml of methyl mercaptan in 100 ml of dry ethylenedichloride at −10° C. to 0° C. The mixture is stirred and allowed to rise gradually to room temperature over a four day period. The mixture is filtered, the filter cake is washed with ethylenedichloride (2×500 ml). The solid is dispersed in 200 ml of H$_2$O, cooled to 5° C. and basified with 6N NaOH solution to give a white oil, which is extracted with CH$_2$Cl$_2$ (3×100 ml). The CH$_2$Cl$_2$ extract is dried (MgSO$_4$) and evaporated to dryness to give 6.41 g of dark green oil. This oil is stirred in HCl/isopropanol and the mixture is evaporated to dryness. The residue is stirred in 35 ml of ethyl ether for 16 hours and filtered to give 3.63 g, mp 178°-181° C. dec. This solid is heated in refluxing ethyl acetate and filtered to give 2.07 g, mp 188°-193° C. Recrystallization from 75 ml of ethylenedichloride affords 1.45 g of the title compound, mp 191°-196° C.

The title compound is also obtained by adding 5-10 fold excess of sodium mercaptide in tetrahydrofuran at 0°-10° C. and by following the above workup.

EXAMPLE 43

In the same manner as described in Example 42, the following thioethers are prepared by substituting methyl mercaptan with the corresponding mercaptans:

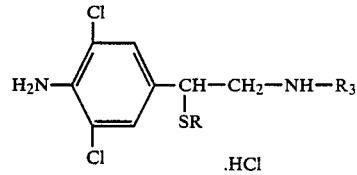

| R | R$_3$ |
|---|---|
| methyl | 2-propyl |
| ethyl | t-butyl |
| 2-propyl | t-butyl |
| n-butyl | t-butyl |
| t-butyl | t-butyl |
| n-hexyl | t-butyl |
| phenyl | t-butyl |
| benzyl | 2-propyl |

EXAMPLE 44

In the manner described in Example 42, substitution of the corresponding chloro compound for N-tert-butyl-3,5-dichloro-β-chloro-4-aminophenethylamine hydrochloride and adding the appropriate mercaptans afford the following thioethers:

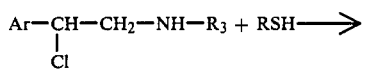

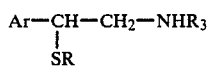

| Ar | R | $R_3$ |
|---|---|---|
| 4-amino-3-cyanophenyl | methyl | 2-propyl |
| 4-methylamino-3,5-dichlorophenyl | methyl | t-butyl |
| 4-amino-3-chloro-5-trifluoromethyl | methyl | t-butyl |
| 4-amino-3-chloro-5-cyanophenyl | methyl | t-butyl |
| 4-amino-3-chloro-5-cyanophenyl | ethyl | t-butyl |
| 4-acetamido-3,5-dichlorophenyl | methyl | t-butyl |
| 4-amino-3-chloro-5-$H_2NCO$—phenyl | methyl | t-butyl |
| 4-amino-3-chloro-5-HOCO—phenyl | methyl | t-butyl |
| 4-amino-3-chloro-5-methylphenyl | ethyl | t-butyl |
| 4-amino-3-chloro-5-methoxyphenyl | n-butyl | t-butyl |
| 4-amino-3-chloro-5-nitrophenyl | methyl | t-butyl |
| 4-amino-3-chloro-5-$CH_3CO$—CO—phenyl | methyl | t-butyl |

EXAMPLE 45

3,5-dichoro-4-(N,N-diethylamino)acetophenone

A sample (2.5 g) of 4-amino-3,5-dichloroacetophenone in 10 ml of acetic anhydride and 25 ml of pyridine is stirred and heated at reflux temperature for 20 hours. The mixture is evaporated to dryness, and the residue is treated with ice and 10% NaOH solution and extracted with $CH_2Cl_2$ (3×50 ml). The extracts are dried ($Na_2SO_4$) and evaporated to dryness to give 2.42 g of semisolid, which is purified by chromatography over $SiO_2$ using $CH_2Cl_2$ as eluent to afford 1.06 g of 4-(N,N-diacetyamino)-3,5-dichloroacetophenone as an oil. This material is dissolved in 10 ml of tetrahydrofuran (THF) under $N_2$ atmosphere and 18 ml of 1M $BH_3$.THF is added dropwise. The mixture is stirred until the reaction is complete and $H_2O$ is added cautiously. The mixture is evaporated to remove THF and 20 ml of $H_2O$ and 10 ml of 10% NaOH are added. This aqueous mixture is extracted with $CH_2Cl_2$ (3×25 ml) and the extracts are dried ($Na_2SO_4$) and evaporated to dryness to yield 0.68 g the desired alcohol. This product (0.3 g) in 2 ml of $CH_2Cl_2$ is added to 0.32 g of pyridinium chlorochromate (PCC) in 2 ml of $CH_2Cl_2$. After 1.25 hours, an additional 0.3 g of PCC is added and after another 0.5 hours, the solution is decanted and the residue is washed with 10 ml of $CH_2Cl_2$. The combined $CH_2Cl_2$ solutions are diluted with 50 ml of $CH_2Cl_2$ and washed with 10 ml of saturated $Na_2CO_3$ solution and 10 ml of $H_2O$ and dried ($Na_2SO_4$). The solution is evaporated to dryness to afford a residue which is chromatographed on $SiO_2$ with $CH_2Cl_2$ as eluent to yield 0.04 g of the title compound as an oil (NMR in $CDCl_3$: δ1.0 (6H, triplet), 2.5 (3H, singlet), 3.25 (4H, quartet), 7.83 (2H, singlet). The monoethylaminoacetophenone is also obtained as a solid (0.12 g) as the second component.

This 3,5-dichloro-ethylaminoacetophenone is further reacted with propionic anhydride, reduced and reoxidized in the above manner to afford 3,5-dichloro-N-ethyl-N-propylaminoacetophenone.

In a similar manner the following 4-(N,N-dialkylamino-acetophenones which are required for preparing 4-(N,N-disubstituted amino) compounds of formula I are prepared:

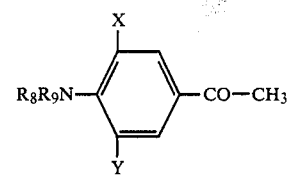

| $R_8$ | $R_9$ | X | Y |
|---|---|---|---|
| n-$C_3H_7$ | n-$C_3H_7$ | Cl | Cl |
| n-$C_4H_9$ | n-$C_4H_9$ | Cl | Cl |
| $C_2H_5$ | n-$C_3H_7$ | Cl | Cl |
| $C_2H_5$ | $C_2H_5$ | Cl | $CH_3$ |
| $C_2H_5$ | $C_2H_5$ | Cl | $CF_3$ |
| $C_2H_5$ | $C_2H_5$ | Cl | $NO_2$ |
| $C_2H_5$ | $C_2H_5$ | Cl | Br |
| $C_2H_5$ | $C_2H_5$ | Cl | $OCH_3$ |

EXAMPLE 46

α-[(tert-butylamino)methyl]-3,5-dichloro-4-diethylaminobenzyl alcohol

In the manner described in Example 29, 3,5-dichloro-4-diethylaminoacetophenone is oxidized with $SeO_2$ and reductively alkylated with t-$BuNH_2$/$NaBH_4$ to afford the title compound, mp 93°–96° C.

Similarly, α-[tert-butylamino)methyl]-3,5-dichloro-4-(n-dipropyl)aminobenzyl alcohol and α-[(tert-butylamino)methyl]-3,5-dichloro-4-(n-dibutyl)aminobenzyl alcohol are prepared.

EXAMPLE 47

2-bromo-3',5'-dichloro-4'-diallylaminoacetophenone and 4'-(allylamino)-2-bromo-3',5'-dichloroacetophenone

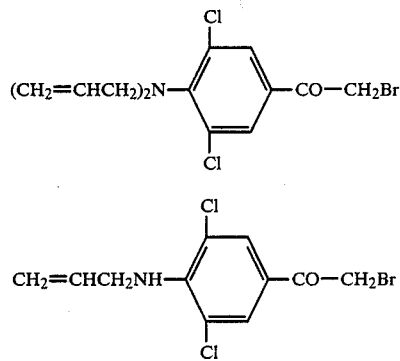

Triethylamine (17.0 g, 0.168 mol) is added in one portion to allyl bromide (105.9 g, 0.875 mol) under a nitrogen atmosphere. The resulting white emulsion gives an exotherm to 70° C. and becomes a thick white solid mass within 5 minutes. The solution formed with the addition of ~100 ml of DMF is stirred for 1 hour at 70°–95° C. A solution of 4'-amino-2-bromo-3',5'-dichloroacetophenone (25.0 g, 0.088 mol) in 50 ml of DMF is added in one portion and the resulting brown reaction mixture is maintained at 80°–90° C. for 2 hours. The progress of the reaction is frequently checked by thin layer chromatography ($SiO_2$/$CH_2Cl_2$/hexanes (1/1)) since prolonged heating results in the decomposition of both starting material and products. The reaction mixture is poured into 1.5 l of $H_2O$ and is stirred for 0.5 hours. After a second aqueous trituration, the residual brown semi-solids are stirred with ~150 ml of $CCl_4$ for 0.5 hours to form a suspension. The yellowish-brown solids are collected by filtration and are air dried to give 14.9 g (59.6%) of recovered phenacyl bromide starting material. The CCl$_4$ filtrate is stirred with MgSO$_4$, filtered and concentrated to yield 9.42 g of a brown syrup. Gradient elution (hexanes/CH$_2$Cl$_2$ (10/0→8/2) flash chromatography on a 9"×2" column of Silica Gel 60 gives two major fractions:

(A) 1.82 g (5.7%) of a faster moving amber syrup, identified as 2-bromo-3',5'-dichloro-4'-diallylaminoacetophenone by IR(neat) 1680 cm$^{-1}$; NMR (CDCl$_3$) δ7.93 (s, 2, AR—H), 6.25–5.55 (complex m, 2, CH═), 5.40–4.95 (complex m, 4, CH$_2$═), 4.40 (s, 2, CH$_2$Br) and 3.87 (m resembling d, 4, J=6 Hz, CH$_2$N); chemical ionization mass spectrum (M+H)$^+$=3.62; and (B) 3.49 g (12.2%) of a slower moving brown syrup, ideitified as 4'-(allyamino)-2-bromo-3',5'-dichloroacetophenone by IR(neat) 3330, 1670 cm$^{-1}$; NMR(CDCl$_3$) δ7.83 (s, 2, AR—H), 6.35–5.65 (complex m, 1, CH═), 5.50–5.00 (complex m, 2, CH$_2$═), 4.84 (br t, 1, NH), 4.37 (s, 2, CH$_2$Br) and 4.20 (br m, 2, CH$_2$N); chemical ionization mass spectrum (M+H)$^+$=322.

EXAMPLE 48

4-(Allyamino)-α-[(tert-butylamino)methyl]-3,5-dichlorobenzyl alcohol

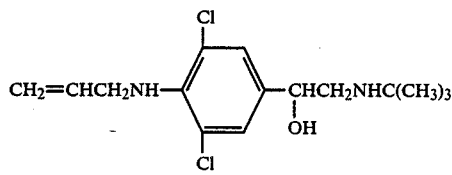

A solution of 4'-(allylamino)-2-bromo-3',5'-dichloroacetophenone (2.88 g, 8.92 mmol) in 10 ml is added dropwise over 1 hour to a stirred solution of t-butylamine (1.34 g, 18.3 mmol) in 20 ml of THF. The reaction temperature is maintained at −24°-13° C. by cooling in a dry ice-CCl$_4$ bath. The resulting amber suspension is warmed to room temperature over 30 minutes and is stirred at 21°-22° C. for 1.5 hours. Sodium cyanoborohydride (2.80 g, 44.6 mmol) is added in two portions over 5 minutes to give a thick tan suspension with an exotherm from 22°-25° C. Glacial acetic acid (∼10 ml) is added dropwise to gradually form a yellow solution which is stirred at room temperature for 3 days. The reaction mixture is poured into a solution of 100 ml of H$_2$O and 100 ml of saturated aqueous NaCl which is then adjusted to pH7 with 10% Na$_2$CO$_3$ and extracted three times with Et$_2$O. The combined extracts are shaken with two portions of diluted aqueous HCl which are combined, neutralized with 10% Na$_2$CO$_3$ to pH8 and extracted three times with Et$_2$O. After stirring the combined extracts with anh. K$_2$CO$_3$, the pale yellow-green solution is filtered and concentrated to yield 2.04 g (72.1%) of a pale yellow syrup, identified as 4-(allylamino)-α-[(tert-butylamino)methyl]-3,5-dichlorobenzyl alcohol by IR(neat) 3400 cm$^{-1}$; NMR(CDCl$_3$) δ7.32 (s, 2, AR—H), 6.35–5.60 (complex m, 1, CH═), 5.45–4.95 (complex m, 2, CH$_2$═), 4.52 (d of d, 1, Ar—CH), 3.97 (overlapping m, 3, Ar—NHCH$_2$), 3.03 (br s, 2, NH and OH), 2.68 (m, 2, CH$_2$N) and 1.13 (s, 9, C(CH$_3$)$_3$); chemical ionization mass spectrum (M+M)$^+$=317. The CH$_2$Cl$_2$/CH$_3$OH/conc. NH$_4$OH (80/19/1)) shows one major spot (R$_f$=0.6) with nine trace impurities. The syrup gradually crystallizes to a tan solid on standing.

EXAMPLE 49

N-tert-butyl-m-hydroxy-β-methylthiophenethylamine hydrochloride

By using the procedure of Example 17 and substituting methyl mercaptan for methanol as in Example 42, the title compound is prepared.

EXAMPLE 50

The following compounds are prepared by the method of Example 29:

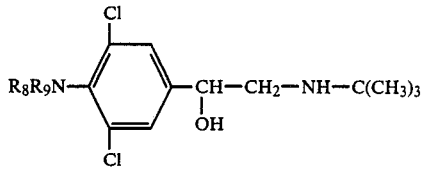

| R$_8$ | R$_9$ | mp °C. |
|---|---|---|
| H | 1-C$_4$H$_9$ | oil |
| H | 1-C$_6$H$_{13}$ | 62–64 |
| H | C$_2$H$_5$ | 209 (HCl salt) |
| H | benzyl | 85–89 |
| H | cyclopentyl | oil |
| H | cyclohexyl | 194–198 (HCl salt) |
| —CH$_2$—CH$_2$—CH$_2$—CH$_2$— | | |

EXAMPLE 51

α-[(tert-butylamino)methyl]-3,5-dichloro-4-diallylaminobenzyl alcohol

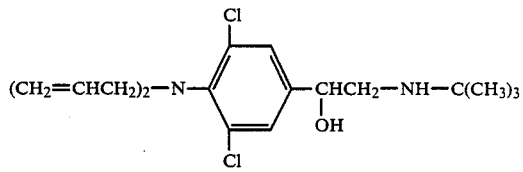

The title compound is prepared using the procedure described for the preparation of 4-(allylamino)-α-[(tert-butylamino)methyl]-3,5-dichlorobenzyl alcohol (Example 44). The pale yellow syrup, which gradually crystallizes on standing, is identified by IR(neat) 3300 and 1630 cm$^{-1}$; NMR(CDCl$_3$) δ7.26 (s, 2, AR—H), 6.23–5.54 (complex m, 2, CH═), 5.32–4.87 (complex m, 4, CH$_2$═), 4.48 (m, 1, Ar—CH), 3.78 (m resembling d, 4, J=6 Hz, Ar—NCH$_2$), 3.4–2.0 (br s, 2, NH and OH), 2.62 (m, 2, CH$_2$N) and 1.13 (s, 9, C(CH$_3$)$_3$); chemical ionization mass spectrum (M+H)$^+$=357, corresponding to that expected of the title compound.

We claim:

1. A compound of the formula

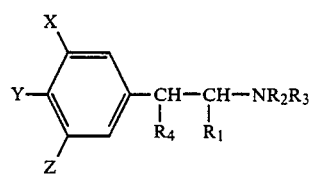

wherein

X is hydrogen, chlorine or bromine;

Y is hydrogen or $NR_8R_9$;

Z is chlorine, bromine, CN;

$R_1$ is hydrogen;

$R_2$ is hydrogen or $C_1$–$C_4$ alkyl;

$R_3$ is hydrogen or $C_1$–$C_4$ alkyl;

$R_4$ is OH, $OR_6$ or $SR_{11}$;

$R_6$ is $C_1$–$C_6$ alkyl, $C_2$–$C_5$ alkanoyl, benzyl, benzoyl or $C_3$–$C_4$ alkenyl;

$R_8$ is hydrogen, $C_2$–$C_4$ alkyl or $C_3$–$C_4$ alkenyl;

$R_9$ is hydrogen or $C_1$–$C_6$ alkyl; with the provisos that when Y is $NH_2$, $NHCH_3$ or $NHC_2H_5$, $R_4$ is $OR_6$ or $SR_{11}$;

when Y is hydrogen, X and Y are halo, $R_2$ is H and $R_3$ is isopropyl, 2-butyl or t-butyl;

when $R_6$ is alkanoyl, $R_2$ and $R_3$ are $C_1$–$C_4$ alkyl, except that when one of $R_2$ or $R_3$ is t-butyl, the other can be either H or $C_1$–$C_4$ alkyl; and when $R_8$ is $C_1$–$C_4$ alkyl, $R_9$ is hydrogen or $C_1$–$C_4$ alkyl; racemic mixtures of the above-identified compounds and the optically active isomers and non-toxic, pharmacologically acceptable acid salts thereof.

2. The compound according to claim 1: α-[(t-butylamino)methyl]-3,5-dichlorobenzyl alcohol hydrochloride.

3. The compound according to claim 1: 4-amino-N-t-butyl-3,5-dichloro-β'-methoxyphenethylamine hydrochloride.

4. The compound according to claim 1: α-[(isopropylamino)methyl]-3,5-dichlorobenzyl alcohol hydrochloride.

5. The compound according to claim 1: α-[(t-butylamino)methyl]-3,5-dibromobenzyl alcohol hydrochloride.

6. The compound according to claim 1: 4-amino-N-t-butyl-3,5-dibromo-β'-methoxyphenethylamine hydrochloride.

7. The compound according to claim 1: N-tert-butyl-3,5-dichloro-β-methoxy-4-methylaminophenethylamine hydrochloride.

8. The compound according to claim 1: α-[(tert-butylamino)methyl]-3,5-dichloro-4-isopropylaminobenzyl alcohol.

9. The compound according to claim 1: 5-[2-(tert-butylamino)-1-hydroxyethyl]-N-propylanthranilonitrile.

10. The compound according to claim 1: 5-[2-(tert-butylamino)-1-hydroxyethyl]-N-isopropylanthranilonitrile.

* * * * *